US006992177B1

(12) United States Patent
Hui et al.

(10) Patent No.: US 6,992,177 B1
(45) Date of Patent: Jan. 31, 2006

(54) SAQUINAVIR DERIVATIVES USEFUL IN IMMUNOASSAY

(75) Inventors: Raymond A. Hui, Indianapolis, IN (US); Gerald F. Sigler, Carmel, IN (US); Richard T. Root, Fishers, IN (US); Wei Yuan, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/009,823

(22) Filed: Dec. 10, 2004

(51) Int. Cl.
*C07K 16/44* (2006.01)
*C07K 17/02* (2006.01)
*C12N 5/12* (2006.01)
*G01N 33/531* (2006.01)
*C07D 217/26* (2006.01)

(52) U.S. Cl. .................. 530/388.9; 530/403; 530/409; 530/809; 435/70.21; 435/436; 546/144; 436/529; 436/815

(58) Field of Classification Search ................ 530/405, 530/409, 809, 388.9, 403; 435/70.21, 436, 435/529, 815; 546/144
See application file for complete search history.

(56) References Cited

U.S. PATENT DOCUMENTS

| 5,508,407 A | 4/1996 | Kaldor et al. |
| 5,679,688 A | 10/1997 | Grobelny |
| 2004/0127689 A1 | 7/2004 | Sigler et al. |

FOREIGN PATENT DOCUMENTS

| EP | 1207394 A2 | 5/2002 |
| WO | WO 93/04043 | 3/1993 |
| WO | WO 93/18006 | 9/1993 |
| WO | WO 03/006506 A2 | 1/2003 |

*Primary Examiner*—Mary E. Ceperley
*Assistant Examiner*—Shafiqul Haq
(74) *Attorney, Agent, or Firm*—Roche Diagnostics Operations, Inc.; Marilyn Amick

(57) ABSTRACT

Analogs of saquinavir functionalized at the quinoline portion of the molecule are described. These include pyridyl analogs (replacing the quinoline ring) with a functional handle out of the ring allowing for elaboration with linkers terminated by a functional group such as an activated ester which are useful for attaching the molecule to other entities such as proteins, polysaccharides, and the like. Analogs of saquinavir derivatized out of the quinoline ring are also described.

15 Claims, 11 Drawing Sheets

SAQUINAVIR DERIVATIVES USEFUL IN IMMUNOASSAY

FIELD OF THE INVENTION

The present invention relates to novel protease inhibitor derivatives useful in immunoassay. More specifically, this invention relates to novel derivatives useful for generating immunogens to the HIV protease inhibitor saquinavir and to novel immunogens useful for producing antibodies to saquinavir, which antibodies are useful in immunoassays for determination of saquinavir in biological samples.

BACKGROUND OF THE INVENTION

HIV protease inhibitors are an important new class of drugs which have made a significant impact on the health care of AIDS patients since the first one, saquinavir, was introduced to the marketplace in 1995. Examples of other protease inhibitors include amprenavir, nelfinavir, lopinavir, ritonavir, and atazanavir. They are especially effective in combination with other anti-HIV drugs such as reverse transcriptase inhibitors or with other HIV protease inhibitors. In spite of remarkable success with these new therapeutic regimens, there are strong indications that results would be much improved if therapeutic drug testing methods were available for monitoring the concentrations of protease inhibitors. Not all patients respond optimally to protease inhibitor combination therapies. Even those who do respond can subsequently develop drug resistance due to the notoriously high rate of mutation of the HIV virus. However, it has been shown that there is a clear relationship between plasma levels of the protease inhibitors and therapeutic efficacy based upon decreased viral load and increased CD4 cell count. One problem lies in the fact that the drugs are metabolized extensively and are subject to complex drug—drug interactions. The results are extremely complex pharmacokinetics and a strong element of unpredictability between dosage and resultant drug levels at any particular time for any particular patient. With therapeutic drug monitoring, drug dosages could be individualized to the patient, and the chances of keeping the virus in check would be much higher. But routine therapeutic drug monitoring of protease inhibitors would require the availability of simple automated tests adaptable to high throughput clinical analyzers. Currently most reports on therapeutic drug monitoring of protease inhibitors have used HPLC methods which are slow, labor-intensive, and expensive. Recently there was a report of a radioimmunoassay (RIA) method for saquinavir (Wiltshire et al., Analytical Biochemistry 281, 105–114, 2000). However, such a method would not be adaptable to high-throughput therapeutic drug monitoring and, like all RIA methods, suffers from the disadvantages of having regulatory, safety and waste disposal issues related to the radioactive isotope label used in the assay. The most desirable assay formats for therapeutic drug monitoring are non-isotopic immunoassays, and such methods have heretofore been unknown for monitoring HIV protease inhibitors.

Saquinavir was developed by Hoffmann LaRoche and approved for use in 1995 under the tradename Invirase. Currently a newer form of saquinavir is sold under the tradename Fortovase, which is better absorbed by the body and thus has a stronger anti-HIV effect than Invirase.

As indicated above, HPLC has been the method of choice for monitoring HIV protease inhibitors. Two recent reports in the literature describe HPLC assays for the simultaneous determination of several protease inhibitors in human plasma, Poirier et al., Therapeutic Drug Monitoring 22, 465–473, 2000 and Remmel et al., Clinical Chemistry 46, 73–81, 2000.

Chemical and biological assays generally involve contacting the analyte of interest with a pre-determined amount of one or more assay reagents, measuring one or more properties of a resulting product (the detection product), and correlating the measured value with the amount of analyte present in the original sample, typically by using a relationship determined from standard or calibration samples containing known amounts of analyte of interest in the range expected for the sample to be tested. Typically, the detection product incorporates one or more detectable labels which are provided by one or more assay reagents. Examples of commonly used labels include functionalized microparticles, radioactive isotope labels such as $^{125}$I and $^{32}$P, enzymes such as peroxidase and beta-galactosidase and enzyme substrate labels, fluorescent labels such as fluoresceins and rhodamines, electron-spin resonance labels such as nitroxide free radicals, immunoreactive labels such as antibodies and antigens, labels which are one member of a binding pair such as biotin-avidin and biotin-streptavidin, and electrochemiluminescent labels such as those containing a ruthenium bipyridyl moiety. Sandwich assays typically involve forming a complex in which the analyte of interest is sandwiched between one assay reagent which is ultimately used for separation, e.g., antibody, antigen, or one member of a binding pair, and a second assay reagent which provides a detectable label. Competition assays typically involve a system in which both the analyte of interest and an analog of the analyte compete for a binding site on another reagent, e.g., an antibody, wherein one of the analyte, analog or binding reagent possesses a detectable label.

Copending U.S. patent application Ser. No. 09/712,525 filed Nov. 14, 2000 having the same assignee as the present application and published as EP 1 207 394 on May 22, 2002, describes a non-isotopic immunoassay for an HIV protease inhibitor comprising incubating a sample containing the inhibitor with a receptor specific for the inhibitor or for a metabolite of said inhibitor and further with a conjugate comprising an analog of the inhibitor and a non-isotopic signal generating moiety. Signal generated as a result of binding of the inhibitor by the receptor is measured and correlated with the presence or amount of protease inhibitor in the original sample. The protease inhibitor conjugates of the present invention are especially useful in such an assay.

Copending U.S. patent application Ser. No. 10/192,052 filed Jul. 10, 2002 having the same assignee as the present application and published as WO 03/006506 on Jan. 23, 2003, describes derivatives of saquinavir derivatized out of the central hydroxyl of the molecule which, when used as either labels or as haptens to form immunogens, gave drug conjugates and antibodies which allowed formation of immunoassays with good dose-response curves to saquinavir. However, high cross-reactivities to saquinavir metabolites were seen.

There remains, among other problems, the need for improved activated haptens, derivatives, and conjugates of the HIV protease inhibitor saquinavir which can be used in immunoassays for determination of saquinavir in biological samples. There is a need, also, for immunogens which permit the development of antibodies specific for saquinavir with low cross-reactivity to saquinavir metabolites. The present invention solves these and other problems.

SUMMARY OF THE INVENTION

It is against the above background that the present invention provides certain unobvious advantages and advancements over the prior art. In particular, the inventor has recognized a need for improvements in saquinavir derivatives useful in immunoassay.

One embodiment of the present invention comprises pyridyl analogs of saquinavir having the structure:

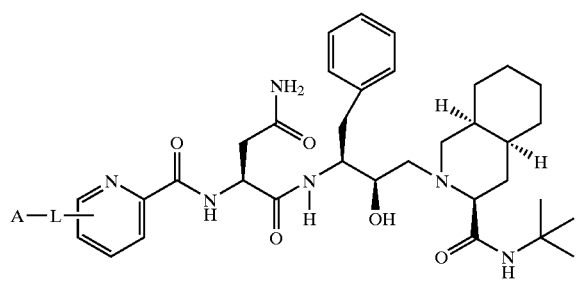

I wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

Another embodiment of the present invention comprises conjugated derivatives of saquinavir having the structure:

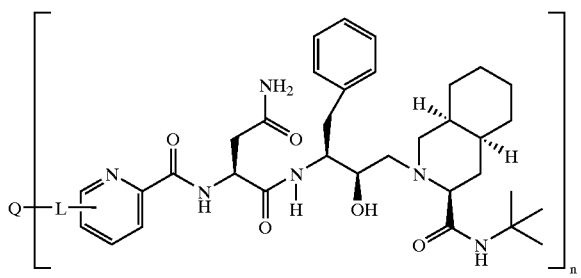

II wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and Q is selected from the group consisting of polypeptides, polysaccharides, synthetic polymers, and non-isotopic labels, and n is a number from 1 to 50 per kilodaltons molecular weight of Q.

Another embodiment of the present invention comprises antibodies derived from an immunogen having the structure:

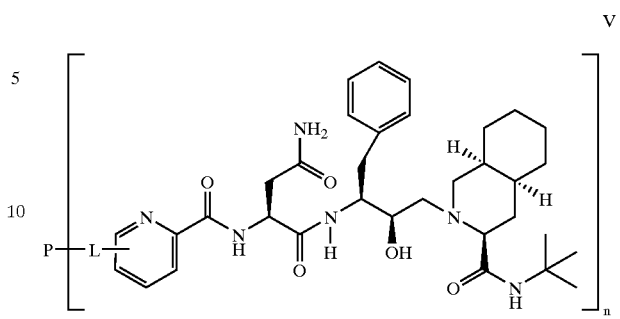

V wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, P is a polypeptide, and n is a number from 1 to 50 per kilodaltons molecular weight of P.

Another embodiment of the present invention comprises derivatives saquinavir having the structure:

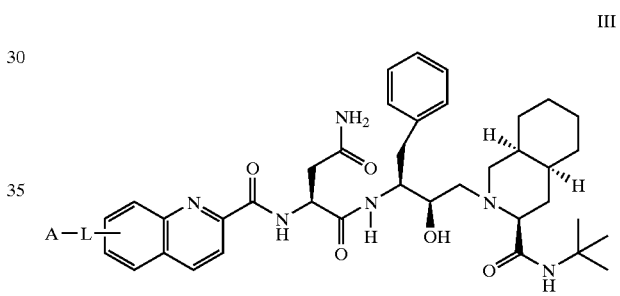

III wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

Another embodiment of the present invention comprises conjugated derivatives having the structure:

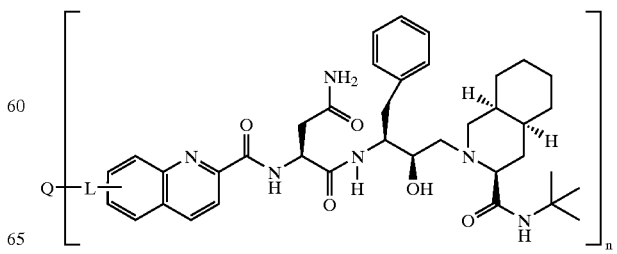

IV wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, Q is selected from the group consisting of polypeptides, polysaccharides, synthetic polymers, and non-isotopic labels, and n is a number from 1 to 50 per kilodaltons molecular weight of Q.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

DETAILED DESCRIPTION OF THE INVENTION

Figure 1:
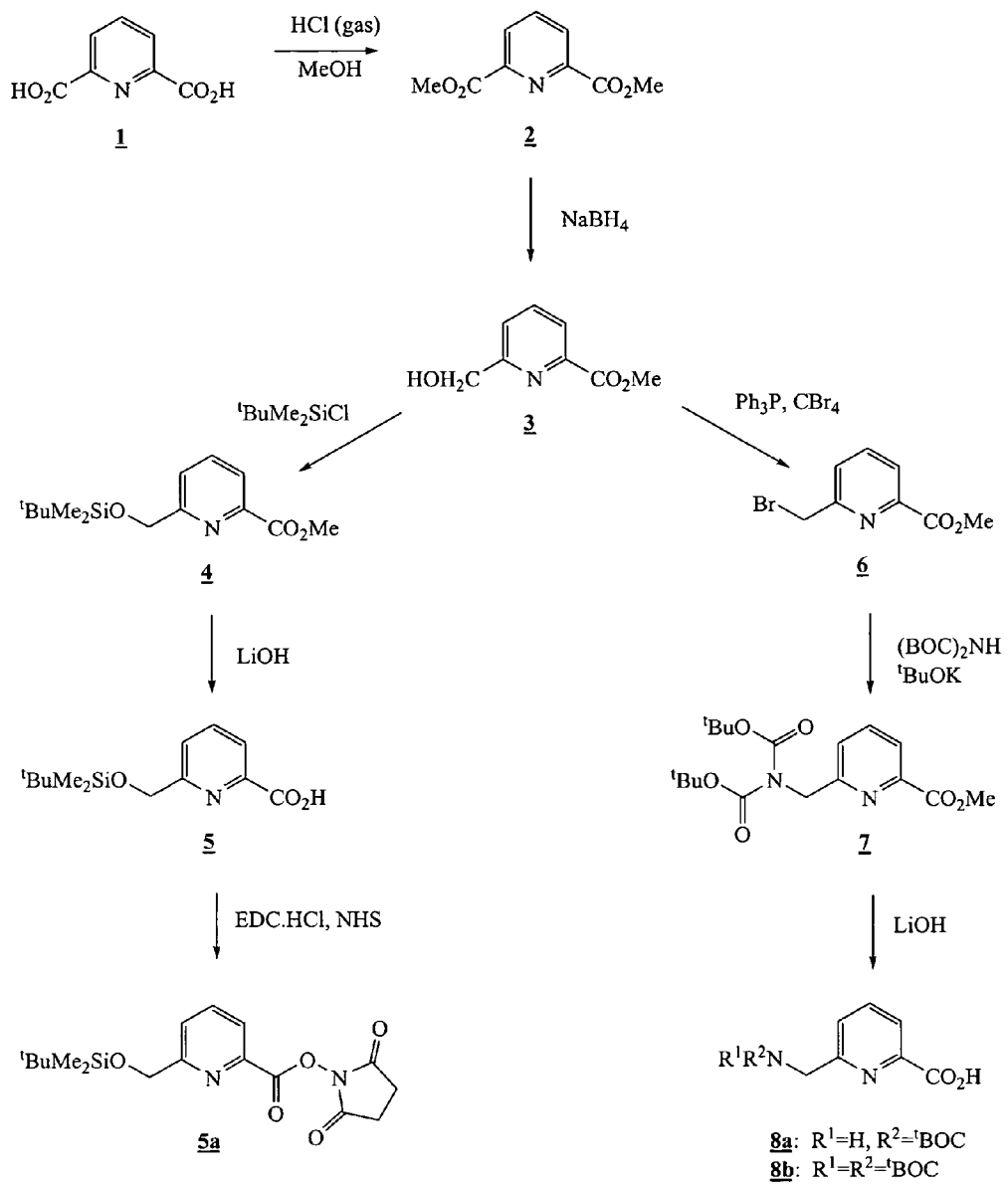
FIG. 1 is a schematic representation showing the synthesis of compounds 5a, 8a, and 8b as described in Examples 1–7.
Figure 2:
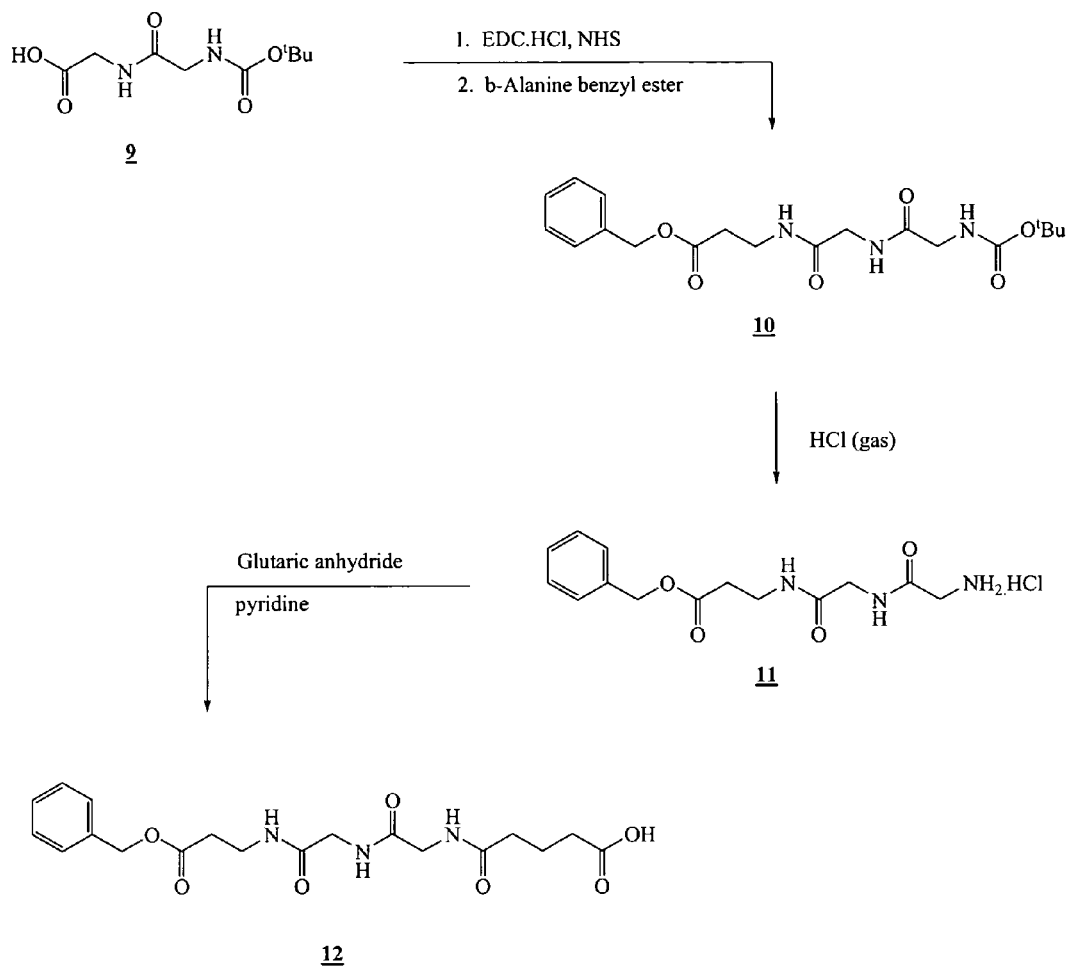
FIG. 2 is a schematic representation showing the synthesis of compound 12 as described in Examples 8–10.
Figure 3:
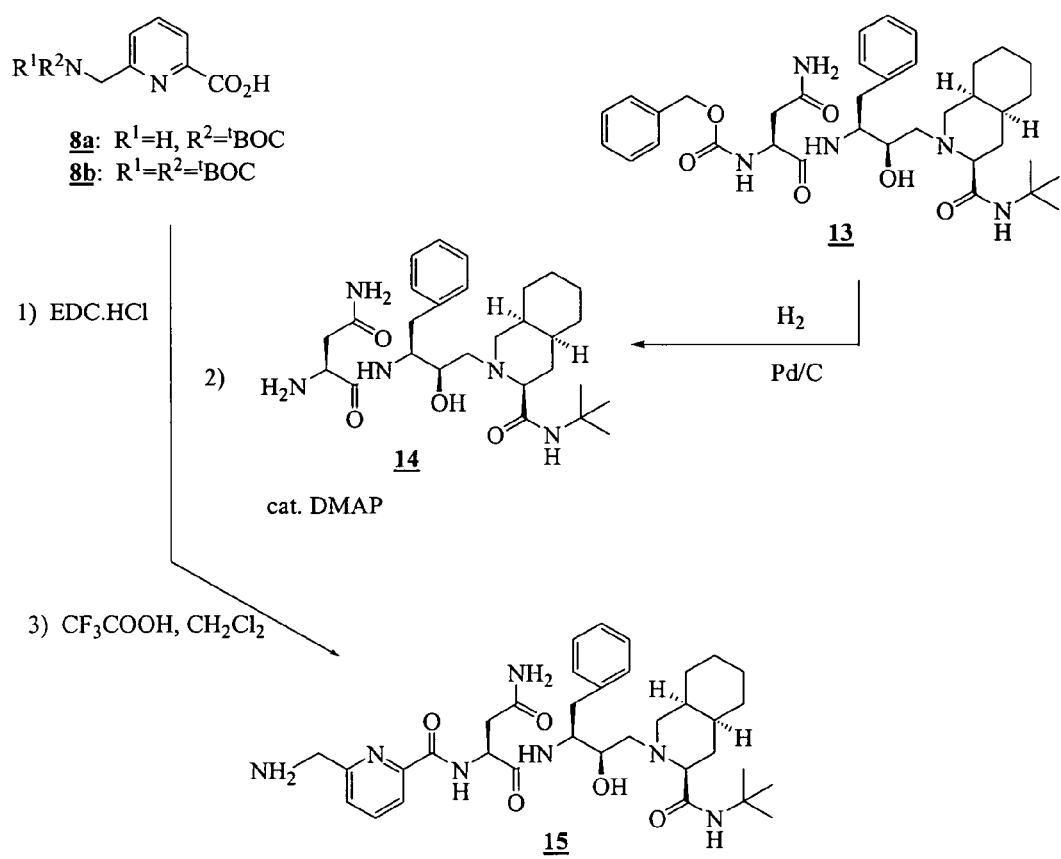
FIG. 3 is a schematic representation showing the synthesis of compound 15 as described in Examples 11 and 12.

In order that the invention may be more readily understood, reference is made to the following examples, which are intended to illustrate the invention, but not limit the scope thereof.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

Saquinavir is represented by the following molecular structure:

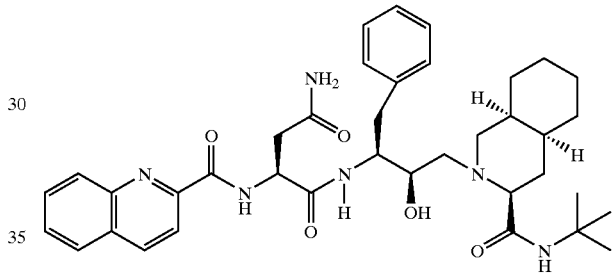

One embodiment of the present invention comprises pyridyl analogs of saquinavir having the following structure:

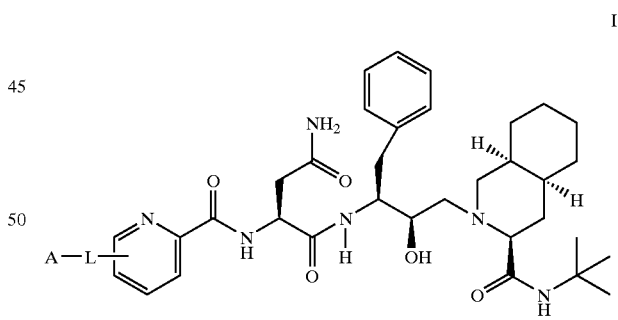

wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

One embodiment of the present invention comprises pyridyl analogs of saquinavir having the following structure:

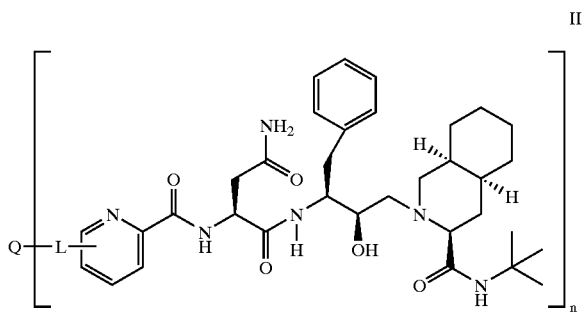

II wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, Q is selected from the group consisting of polypeptides, polysaccharides, synthetic polymers, and non-isotopic labels, and n is a number from 1 to 50 per kilodaltons molecular weight of Q.

Another embodiment of the present invention comprises antibodies derived from an immunogen having the structure:

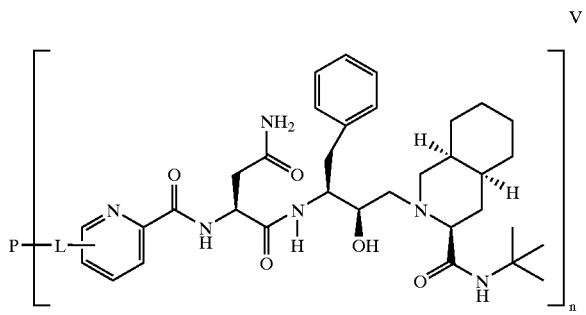

V wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, P is a polypeptide, and n is a number from 1 to 50 per kilodaltons molecular weight of P.

Another embodiment of the present invention comprises derivatives saquinavir having the following structure:

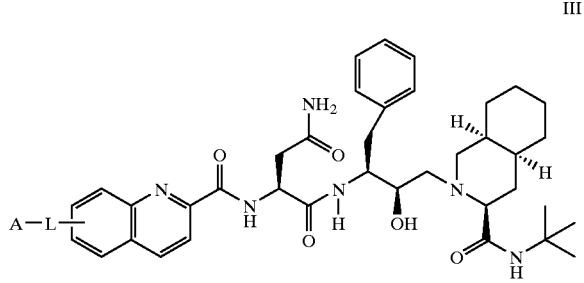

III wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

Another embodiment of the present invention comprises conjugated derivatives having the structure:

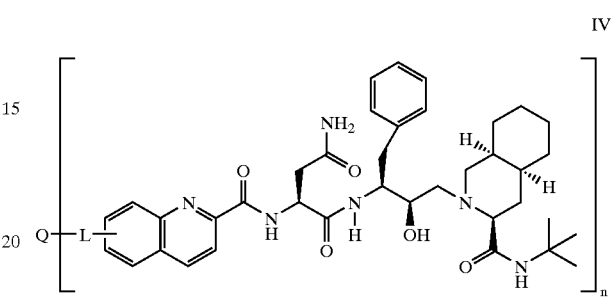

IV wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, Q is selected from the group consisting of polypeptides, polysaccharides, synthetic polymers, and non-isotopic labels, and n is a number from 1 to 50 per kilodaltons molecular weight of Q.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

Throughout the specification, numbers in boldface type are used refer to chemical structures illustrated in the drawings.

As used herein, analyte refers to a substance, or group of substances, whose presence or amount thereof is to be determined.

Antibody means a specific binding partner of the analyte and is any substance, or group of substances, which has a specific binding affinity for the analyte to the essential exclusion of other unrelated substances. The term includes polyclonal antibodies, monoclonal antibodies and antibody fragments.

Haptens are partial or incomplete antigens. They are protein-free substances, mostly low molecular weight substances, which are not capable of stimulating antibody formation, but which do react with antibodies. The latter are formed by coupling a hapten to a high molecular weight carrier and injecting this coupled product into humans or animals. Examples of haptens include therapeutic drugs such as digoxin and theophylline, drugs of abuse such as morphine and LSD, antibiotics such as gentamicin and vancomycin, hormones such as estrogen and progesterone, vitamins such as vitamin B12 and folic acid, thyroxin, histamine, serotonin, adrenaline and others.

An activated hapten refers to a hapten derivative that has been provided with an available site for reaction, such as by the attachment of, or furnishing of, an activated group for synthesizing a derivative conjugate.

The term linker refers to a chemical moiety that connects a hapten to a carrier, immunogen, label, tracer or another linker. Linkers may be straight or branched, saturated or unsaturated carbon chains. They may also include one or more heteroatoms within the chain or at termini of the chains. By heteroatoms is meant atoms other than carbon which are chosen from the group consisting of oxygen, nitrogen and sulfur. The use of a linker may or may not be advantageous or needed, depending on the specific hapten and carrier pairs.

A carrier, as the term is used herein, is an immunogenic substance, commonly a protein, which can join with a hapten, thereby enabling the hapten to stimulate an immune response. Carrier substances include proteins, glycoproteins, complex polysaccharides and nucleic acids that are recognized as foreign and thereby elicit an immunologic response from the host.

The terms immunogen and immunogenic as used herein refer to substances capable of producing or generating an immune response in an organism.

The terms conjugate and derivative refer to a chemical compound or molecule made from a parent compound or molecule by one or more chemical reactions.

As used herein, a detector molecule, label or tracer is an identifying tag which, when attached to a carrier substance or molecule, can be used to detect an analyte. A label may be attached to its carrier substance directly or indirectly by means of a linking or bridging moiety. Examples of labels include enzymes such as β-galactosidase and peroxidase, fluorescent compounds such as rhodamine and fluorescein isothiocyanate (FITC), luminescent compounds such as dioxetanes and luciferin, and radioactive isotopes such as $^{125}$I.

The term active ester within the sense of the present invention encompasses activated ester groups which can react with nucleophiles such as, but not limited to, free amino groups of peptides, polyaminoacids, polysaccharides or labels under such conditions that no interfering side reactions with other reactive groups of the nucleophile-carrying substance can usefully occur.

The compounds of the present invention in a general sense may be made by the coupling of the precursor partial saquinavir moiety, as exemplified by the amine intermediate 14 (see, e.g., EP 1 207 394) and as shown in FIGS. 3, 5, 9, and 11, with a suitably substituted pyridine or quinoline intermediate, either of which also carries a carboxylic acid group or an activated form thereof which is capable of reacting readily with the terminal amine of the intermediate 14. For example, compounds of structure I may be obtained by coupling intermediate 14 with a pyridine intermediate that is substituted firstly with a carboxylate or activated carboxylate group at the position ortho- to the ring nitrogen, and secondly with another group G. The coupling may be achieved by means of a suitable coupling agent such as, but not limited to, a carbodiimide when the coupling is performed with the carboxylic acid. As an alternative, an active ester may be formed from the carboxylic acid and such an ester allowed to react with the amine of intermediate 14. The second substituent group G of the pyridine may be located at any of the other free positions of the ring nucleus, and may comprise either carbon atoms or heteroatoms or both, arranged in a straight or branched chain, so long as it carries on itself a suitable activated functionality, or a masked active functionality which may be converted to its active form, which may be used to react with yet additional suitable moieties to produce the overall linker L carrying the final active functionality A as shown in FIG. 1. Such a process may also be usefully described as linker extension, and many variations of the process are well known to practitioners in the art. In many cases the group G may comprise the linker L, with the activated functionality A or the masked equivalent already present, such as, for example, an alkyl ester which may then be hydrolyzed to the acid and converted to an active ester using methods well known in the art.

In a similar manner, compounds of structure III may be obtained by coupling intermediate 14 with a quinoline intermediate that is substituted in the same way as described above for the pyridine intermediate.

Figure 4:
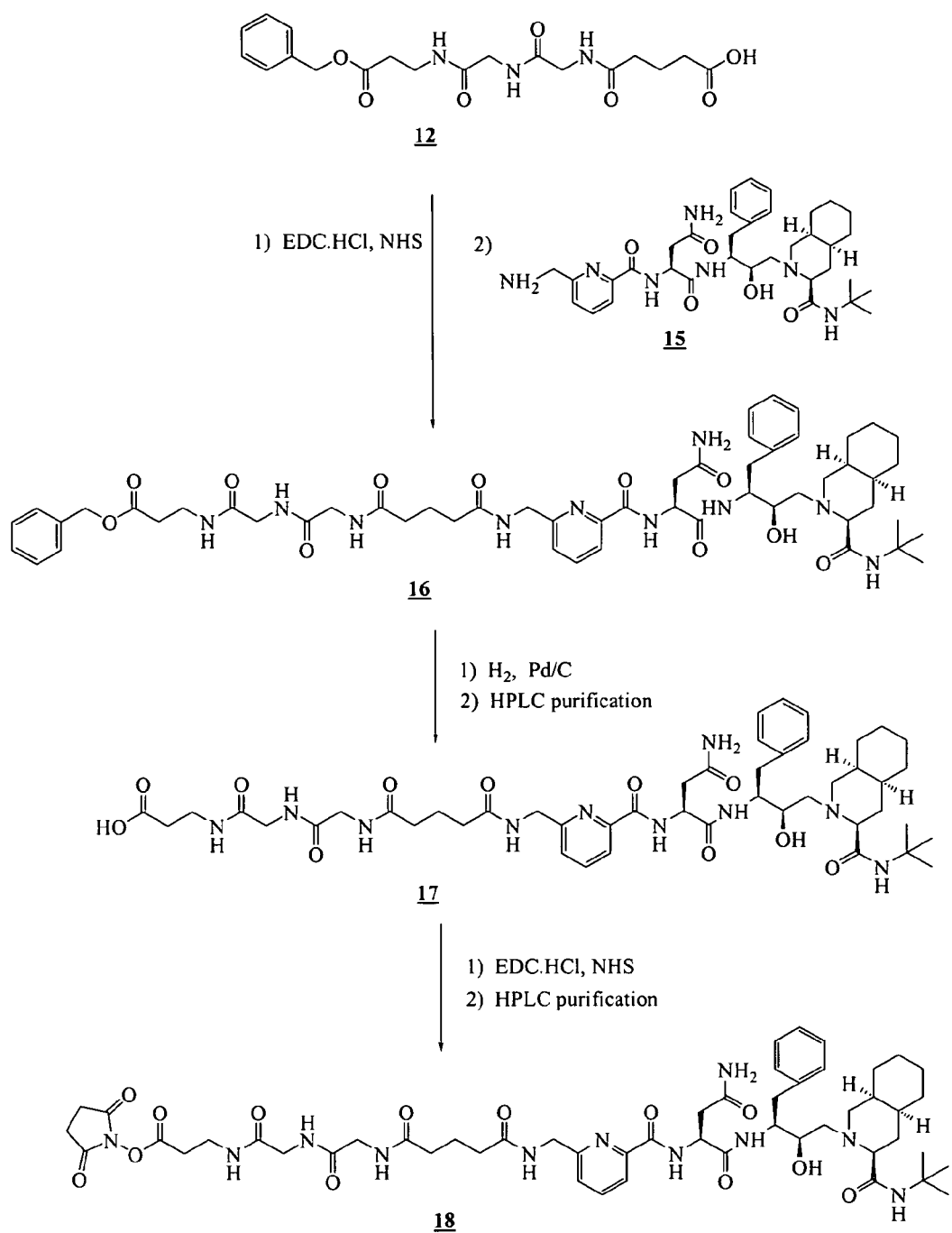
FIG. 4 is a schematic representation showing the synthesis of compound 18 as described in Examples 13 and 14.
Figure 5:
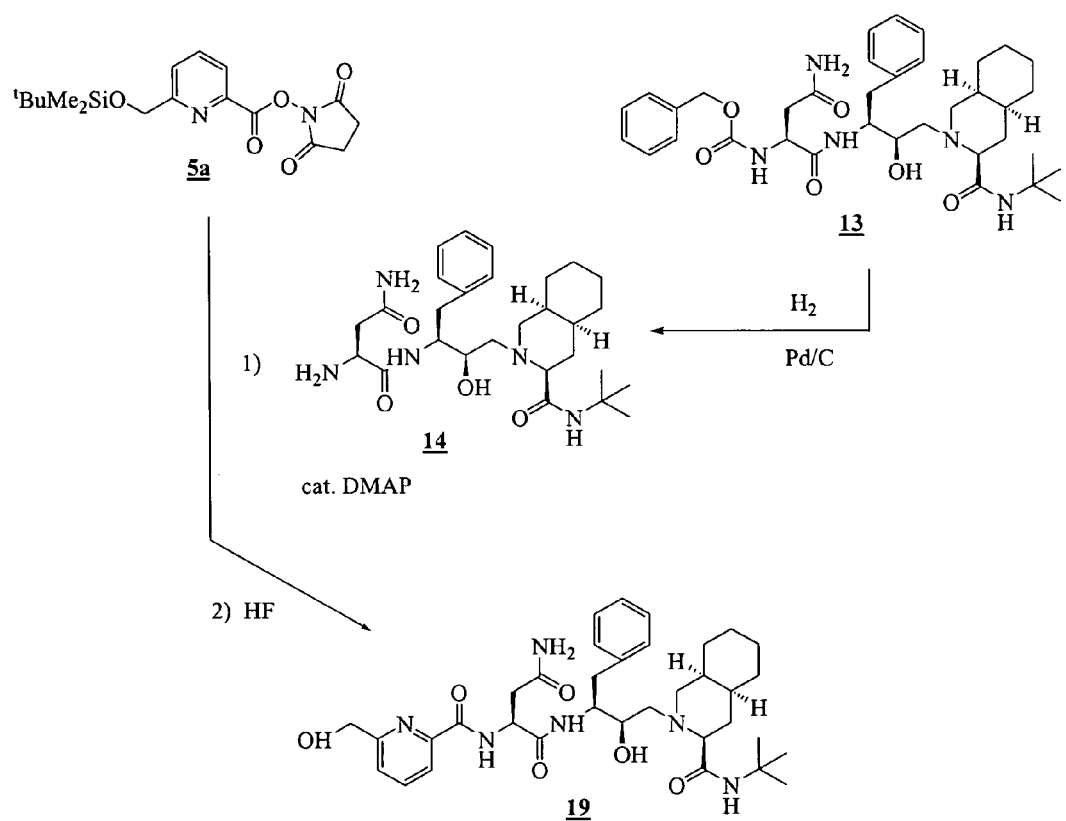
FIG. 5 is a schematic representation showing the synthesis of compound 19 as described in Example 15.

Preferred groups G are those which are amenable to conversion to a functionality such as an amine or thiol which react preferentially with further suitable bifunctional moieties over the central hydroxy of the core structure of saquinavir or the saquinavir-pyridyl analog. For example, an amine and in particular an alkyl amine would possess greater reactivity over the central hydroxy towards active esters or haloalkyl moieties and coupling of the amine with the bifunctional moiety may be accomplished with minimal reaction at the central hydroxy. Particularly preferred are alkylamino groups and their protected equivalents, such as the aminomethyl group and the tert-BOC protected aminomethyl group, as exemplified by compounds 8a and 8b and the resulting compound 15 subsequently obtained. Examples of preferred bifunctional moieties which may be used to extend the linker moiety include aminoalkanoates, such as aminocaproate wherein the amino group is masked with a protecting group readily removed under mild conditions; or short peptides, such as the glycyl-glycyl-β-alanine exemplified in FIG. 7; or an alkyldioic acid chloride active ester, such as the glutarate linker exemplified by compound 34 in FIG. 10; or an aryldioic acid active ester, such as is exemplified by compound 28 in FIG. 6; or a peptide-alkanoate moiety such as exemplified by compound 12 in FIG. 4.

In many cases the greater steric hindrance at the central hydroxy is sufficient to allow useful reaction at the group G without needing to protect the central hydroxy. In some cases, for example where group G is a hydroxy or a hydroxyalkyl wherein the reactivity is expected to be about the same as the central hydroxy of the core saquinavir moiety, selectivity may be achieved by protecting the central hydroxy, for example as a benzoyl ester or a trichloroacetate or the like, prior to deprotecting the hydroxy or hydroxyalkyl in group G followed by linker extension by means of reaction with a suitable bifunctional moiety such as one containing an acid chloride to form an ester bond, or an isocyanate to form an urethane bond, followed by deprotection of the central hydroxy group of the saquinavir or saquinavir-pyridyl core moiety.

The sequence of such protection and deprotection steps are well known to those skilled in the art, and many examples of such steps and other suitable protective groups for amines, hydroxys and thiols may be found in the literature, such as may be found in "*Protective groups in Organic Synthesis*", 2$^{nd}$ Edition, T. Greene & P. Wuts, Wiley-Interscience, 1991. The protecting group is preferably one which is removed under mildly basic or acidic conditions so as not to affect the integrity of the bonds or other moieties in the saquinavir or saquinavir-pyridyl radical. An example of an N-protecting group removed under mildly basic conditions is fluorenylmethyloxycarbonyl (FMOC).

An example of an N-protecting group easily removed with acid is t-butyloxycarbonyl (BOC). Many other suitable N-protecting groups as well as O-protecting and S-protecting groups are well known in the art and are exemplified in Greene & Wuts. ibid.

As an example, the compound 8a, as shown in FIG. 1, carries a masked amine functionality corresponding to group G as described above as well as a carboxylic acid group. Coupling to the intermediate 14 followed by unmasking of the amine comprised within G then furnishes compound 15 which is then reacted with another suitable moiety—in this case the protected peptide 12—to give a compound of structure I carrying the overall linker L with a protected or masked terminal active functionality, which is itself then unmasked and converted to the active functionality A using methods known to those skilled in the art and as exemplified in FIGS. 3 and 4 and in Examples 15 through 18. Other non-limiting examples of group G may include haloalkyl, cyanoalkyl, alkylcarboxylate esters, or alkyl or aryl groups carrying others such as are selected from A.

Figure 6:
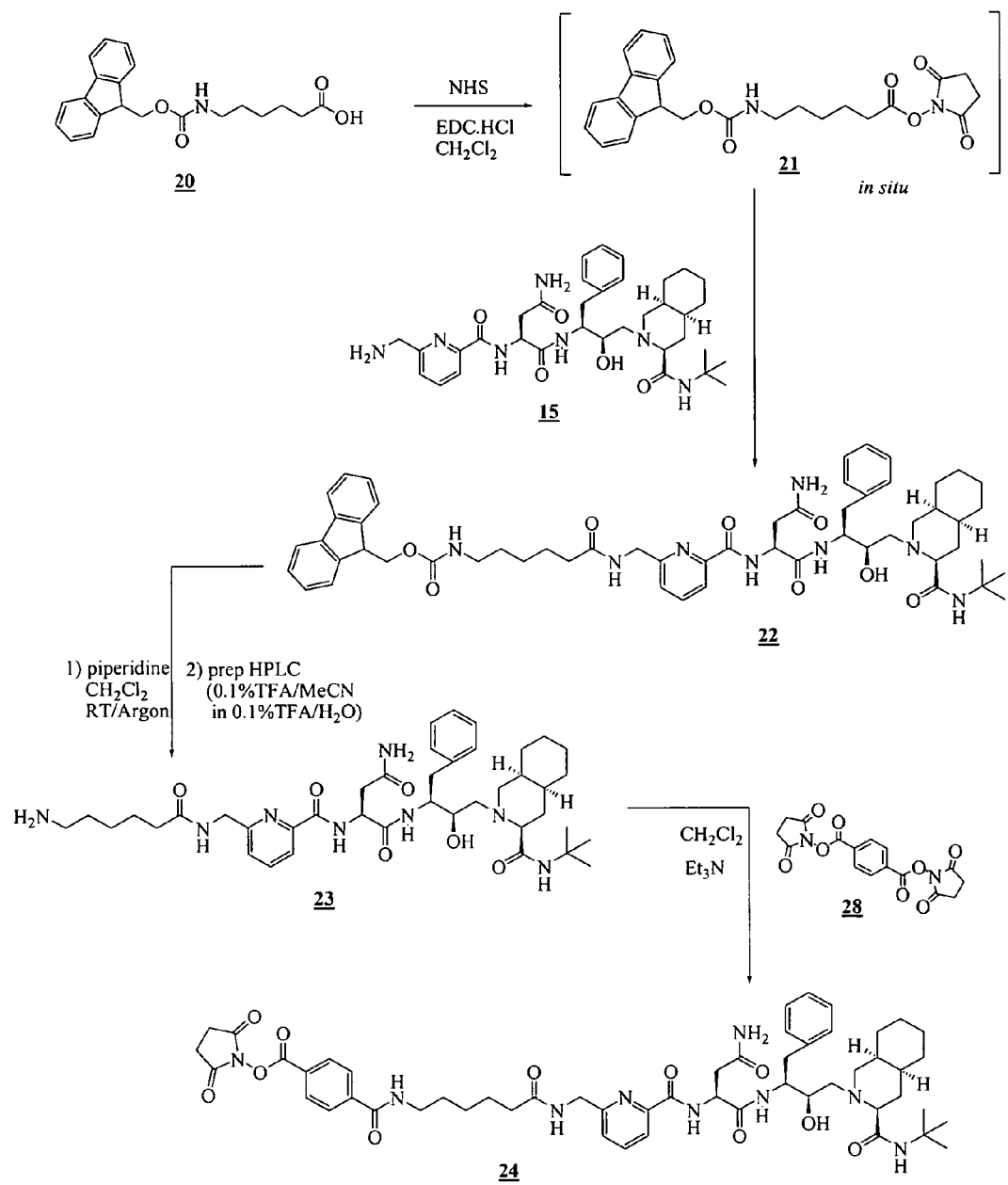
FIG. 6 is a schematic representation showing the synthesis of compound 22 as described in Example 16 and the synthesis of compound 24 as described in Example 18.
Figure 7:
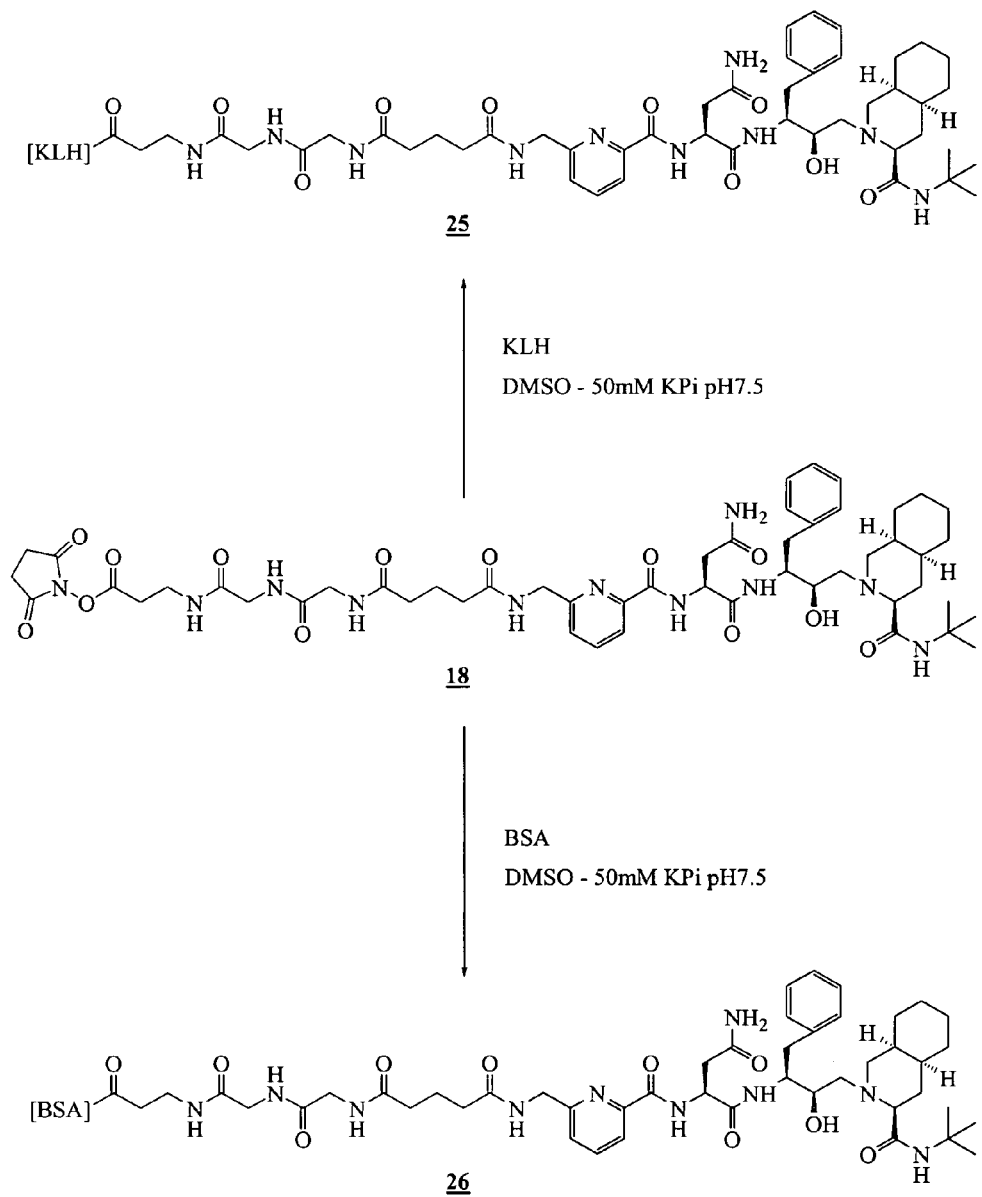
FIG. 7 is a schematic representation showing the synthesis of the saquinavir-KLH conjugate 25 as described in Example 19 and the synthesis of the saquinavir-BSA conjugate 26 as described in Example 20.

Another example is where the aminomethyl or aminoalkyl group comprising group G and as exemplified by compound 15 may be reacted with a bifunctional moiety such as an aminocaproate active ester wherein the amine is protected to form an extended linker followed by deprotection of the terminal amine and reaction with another bifunctional moiety such as phthalic acid di-(N-hydroxysuccinimide) diester 28 to form the extended linker L carrying a terminal active functionality A, and as illustrated by compound 24 and as shown in FIG. 6 and in Examples 16 through 18.

Other suitable functionalities will be readily suggested to practitioners skilled in the art. As a further illustration, haloalkyl groups G may be reacted with an amine-containing moiety carrying a further functionality such as an alkyl ester to form an extended linker comprising L and the ester hydrolyzed to the acid and converted to an active ester to form A. Cyanoalkyl groups may be hydrogenated to form an amine, or hydrolyzed to an iminoester, which may then be reacted with a further moiety such as the amine-alkyl ester moiety described in the previous sentence and carried forwards to the compound comprising L and A. Another example of a group G may be a nitro group, which may then be reduced to the amine which may then be reacted with a suitable bifunctional moiety such as one containing an acid chloride, or an alkylhalide wherein the halide is bromo or iodo, or an aldehyde under reducing conditions such as in the presence of borohydride, to furnish intermediates with an extended linker. Yet another example of a group G may include a masked thiol, such as an acetylthioalkyl, which is then deprotected under mild basic conditions and the free thiol reacted with a bifunctional moiety containing a maleimide or another thiol-reactive functionality to provide an extended linker. Alternatively, G may include a maleimido group, which may then be reacted with another bifunctional moiety containing a thiol to furnish an extended linker. A yet further example may include a hydroxy or hydroxyalkyl which may be protected with a suitable group such as a t-butyldimethylsilyl group or the like, which is then deprotected and then coupled with another bifunctional moiety such as one containing an acid chloride to give an extended linker. Other suitable transformations and couplings will be readily apparent to those skilled in the art.

Figure 9:
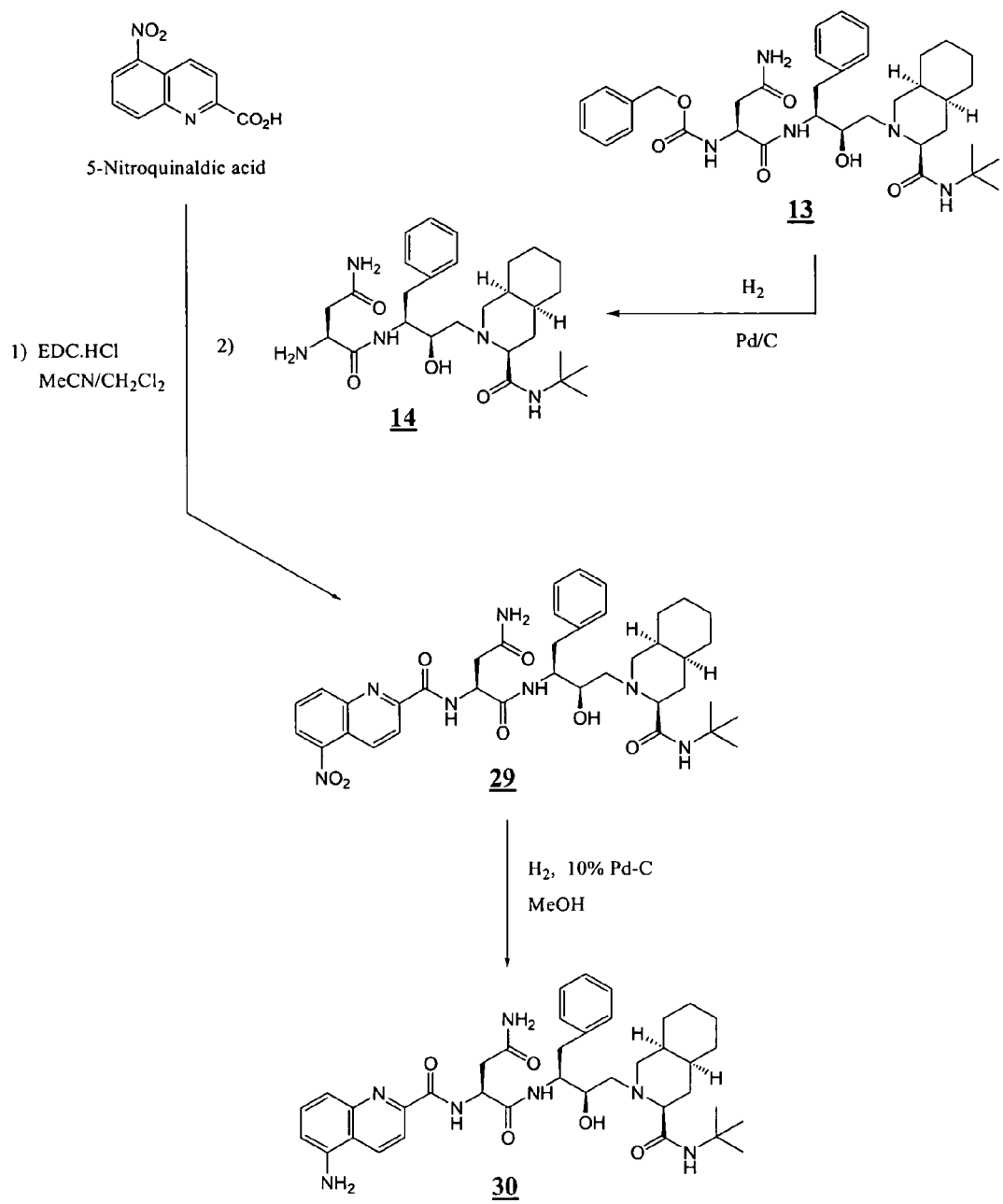
FIG. 9 is a schematic representation showing the synthesis of compound 30 as described in Examples 24 and 25.
Figure 10:
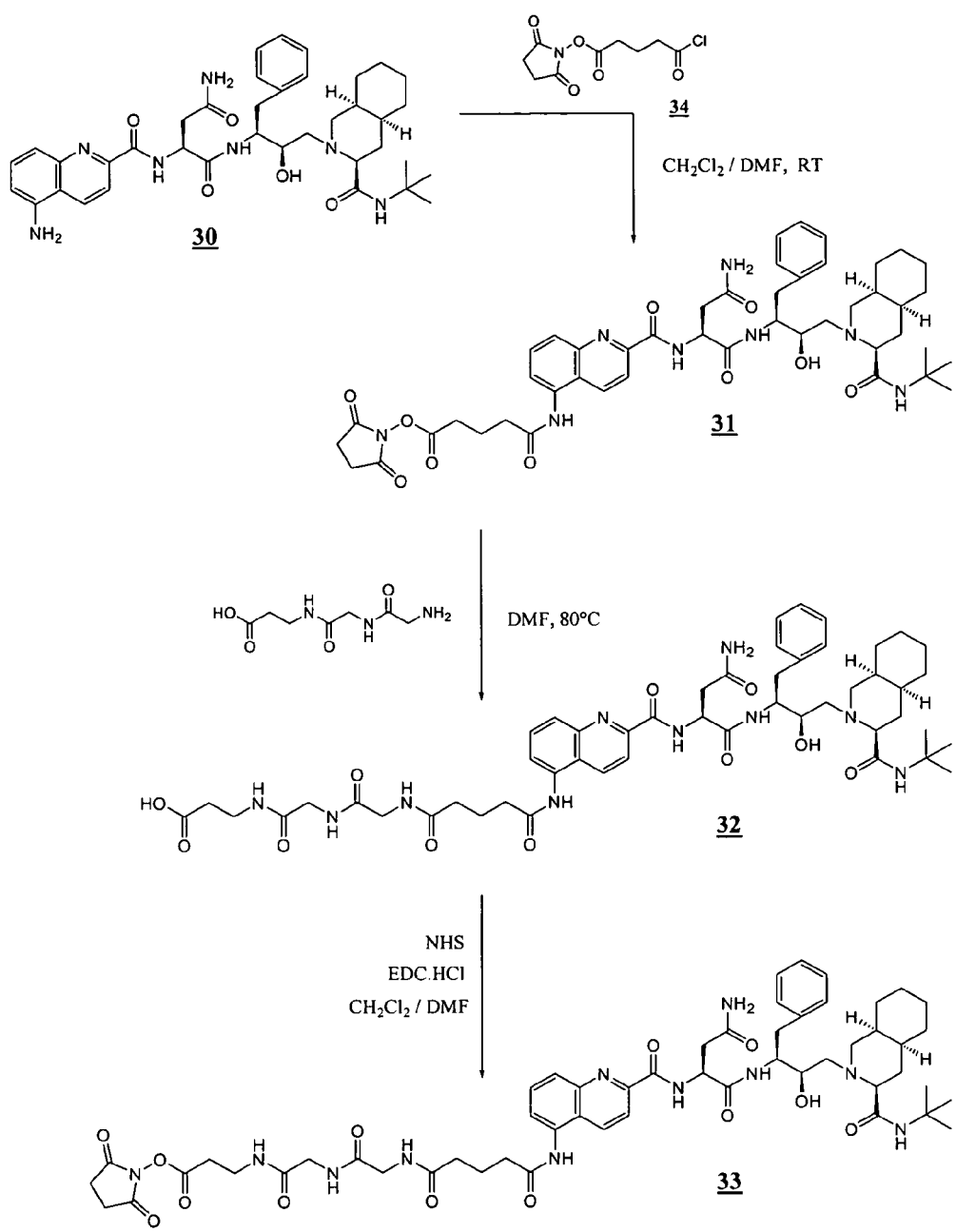
FIG. 10 is a schematic representation showing the synthesis of compound 33 as described in Examples 26–28.
Figure 11:
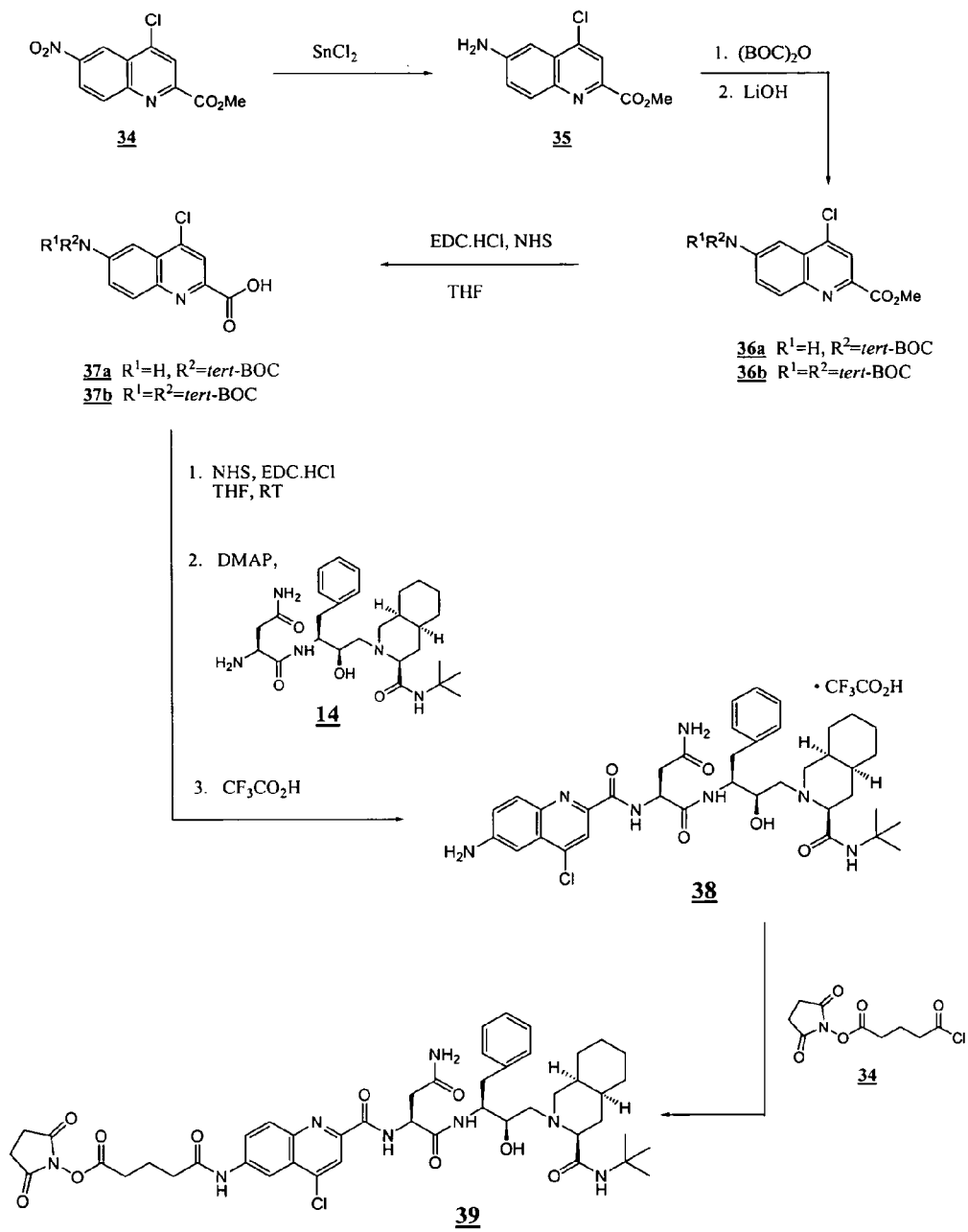
FIG. 11 is a schematic representation showing the synthesis of compound 39 as described in Examples 29–31.

A yet further example of such transformations may be seen in FIGS. 9 and 10, wherein a group G comprising a nitro group is present in the quinoline derivative that is coupled to compound 14 to form compound 29. The nitro group is then reduced to the amine which is then reacted with a suitable bifunctional moiety such as the glutarate acid chloride N-hydroxysuccinimide ester to form compound 31 comprising a compound of structure III carrying a linker L with an active functionality A. Such compounds may be extended, also as exemplified in FIG. 10, with yet another bifunctional linker such as the peptide shown, followed by conversion of the carboxylate at the terminal to an active ester, to furnish compound 33, also comprising a compound of structure III carrying a linker L with an active functionality A, as shown in FIG. 10.

The linker L serves the purpose of providing an additional spacer between the terminal activated functionality A and the saquinavir or saquinavir-pyridyl analog moiety. Linker length and composition are well known to those skilled in the art to have effects on immunogen response and conjugate performance. There are many examples of commercially available or easily synthesized linkers in the literature for use in the present case to extend group G to furnish the eventual linker L. For a good treatise on this subject, the reader is referred to *Bioconjugate Techniques*, G. Hermanson, Academic Press, 1996. In some cases the linker L may be dispensed with and the saquinavir or saquinavir-pyridyl analog moiety directly attached to an activated functionality A.

Compounds of structure I or III may then be conjugated through their active functionality A to detector molecules or labels, for example an enzyme such as galactosidase or peroxidase, or to fluorescent labels such as fluorescein or rhodamine or Cy-5 or the like, or to luminescent labels such as luciferin or the like, or to polysaccharides such as aminodextran or the like, or to other synthetic polymers such as polylysine or the like, to furnish compounds of structure II and IV. Additionally, these compounds may be conjugated through their active functionality A to other moieties carrying radioactive isotopes such as $^{125}$I or the like to furnish compounds analogous to structure II and IV but which now possess an isotopic label. Typically, such coupling is achieved through the use of complementarily reacting functional groups, such as the reaction of the amino groups of the lysines of an enzyme with compounds wherein A is an active ester to form a stable amide bond, or with compounds wherein A is an isothiocyanate or isocyanate to form the corresponding thiourea or urea bond. Other suitable combinations will be apparent to one skilled in the art. These reactions may typically be carried out under relatively mild conditions such as in a suitable organic solvent such as DMSO or DMF or the like with or without the addition of an aqueous component as a cosolvent, and at mild temperatures generally from 0° C. to less than 100° C. and typically around room temperature or so.

Figure 8:
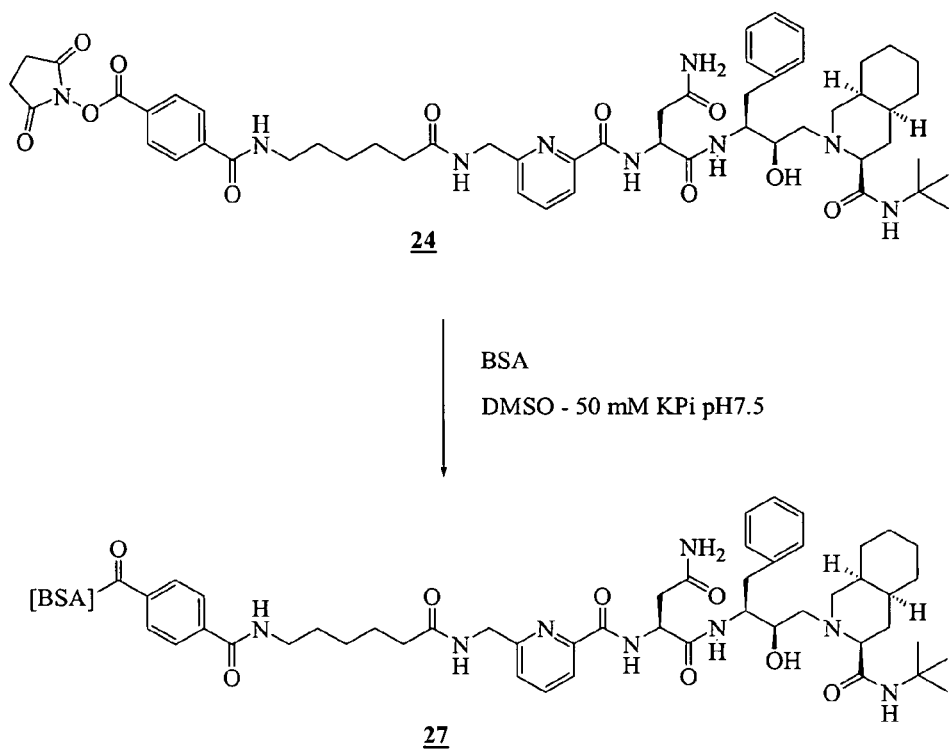
FIG. 8 is a schematic representation showing the synthesis of the saquinavir-BSA conjugate 27 as described in Example 21.

Similarly, compounds of structure I, which may also be termed an activated hapten in the present case, may then be conjugated through their active functionality A to polypeptides, such as proteins, to furnish compounds of structure V. In a similar way, compounds of structure III may be conjugated to similar components to give analogous compounds as the foregoing. Typically, such coupling is achieved through the use of complementarily reacting functional groups, such as the reaction of the amino groups of the lysines of a protein with compounds wherein A is an active ester to form a stable amide bond. The conjugation with polypeptides, in particular proteins well-known as immunogenic carrier substances, furnishes conjugates which are useful as immunogens. These immunogens are then used to immunize animals such as mice to obtain antibodies using methods well known in the art. The immunogenic carrier is typically a polypeptide or a polysaccharide with a molecular weight more than 10 kD. Preferred immunogenic carriers are polypeptides with a molecular weight more than 100 kD. Examples of preferred carrier substances are keyhole limpet hemocyanin (KLH), Limulus polyphemus hemocyanin (LPH) and bovine thyroglobulin (BTG). Other useful polypeptides include albumins, such as bovine serum albumin (BSA), which provide conjugates that may be used in screening assays such as ELISA assays, or even as immunogens, depending on the amount of the drug moiety that is conjugated to the polypeptide. The reaction between the activated hapten and amino groups on the carrier is typically carried out in a buffered mixture of water and a water miscible organic solvent such as DMSO at room temperature for 0.5 to 5 days. The pH of the buffer is typically between 6 and 8 for active esters, isocyanates, and isothiocyanates, or between 7 and 10 for imidates, and is adjusted according to the known reactivity of the carrier amino groups and the activated functionality. In the case where the terminal group A is a maleimide, the reactive groups on the carrier are thiols. These thiol groups are either native to the carrier or may be introduced using thiolating reagents such as 2-IT or SATP. The optimum pH for the conjugation of maleimides to thiol groups to give thioethers is typically between 5 and 7. Following the reaction, the immunogen is dialyzed or subjected to size exclusion chromatography in order to remove unconjugated hapten and organic solvent. An alternative method of obtaining immunogens is to react an activated hapten wherein A is aldehyde with the amino groups of a carrier protein or polypeptide to form a Schiff base, followed by reduction with mild reducing agents such as a cyanoborohydride, to form a stable amine bond. Variations on this last approach will also be suggested to those skilled in the art to which the present invention belongs. Other suitable combinations will be apparent to one skilled in the art. Examples of the conjugation of compounds of structure I with immunogenic carrier substances may be seen in FIGS. 7 and 8.

SPECIFIC EMBODIMENTS

In the examples that follow, boldface, underlined numbers refer to the corresponding structure in the drawings.

Flash chromatography was carried out on silica gel 60 (230–400 mesh, EM Science). Thin layer chromatography was performed on silica gel plates (0.25 mm, EM Science, Cat. # 5717-5) and visualized under an ultraviolet lamp.

Solvents were obtained from J.T. Baker Company unless otherwise stated. Ethyl acetate (EtOAc), hexanes (hex) methanol (MeOH), and Methylene Chloride ($CH_2Cl_2$) were used as received for chromatography and reaction work-ups. Dry $CH_2Cl_2$ was obtained by boiling over calcium hydride under argon and under reflux. Dry tetrahydrofuran (THF) was obtained by boiling over sodium-benzophenone under argon and under reflux. Dry dimethylformamide (DMF) and dry dimethylsulfoxide (DMSO) were obtained in Sure/Seal™ bottles from Aldrich Chemical Company.

Reagents and chemicals were obtained from either Sigma-Aldrich Chemical Company or from Fluka Chemicals unless otherwise stated.

Proton nuclear magnetic resonance spectra ($^1$H-NMR) were obtained on a Varian Gemini 2000 (200 MHz) equipped with a Sun/Sparc work station. All NMR chemical shift values are reported in δ units (ppm) referenced with respect to residual solvent. The abbreviations used are: s, singlet; d, doublet; t, triplet; br, broad.

Liquid chromatography mass spectra (LC-MS) were obtained on an Agilent HP 1100 LC/MS system equipped with a diode array detector and quaternary pump with the chromatographic stream ported post-column into the MSD detector. Unless otherwise stated, the analytical column used was a Vydac 218TP54 analytical column (300 Å, 5$\mu$) equipped with a Phenomenex guard module (KJO-4282). Unless otherwise stated, runs were performed using 0.1% TFA-MeCN(C) in 0.1% TFA-$H_2O$ (A) with a solvent gradient of 5% (0 min) to 100% (20 min) to 5% (25 min) of (C) in (A).

Preparative reverse phase HPLC (RP-HPLC) was performed using two Varian/Rainin SD-1 pumps with Varian/Dynamax radial compression columns (C18, Microsorb 60-8). A gradient of 15% (0 min) to 85% (20 min) of (C) in (A) with a flow rate of 20–40 mL/min was used.

EXAMPLE 1

Synthesis of Compound 2

HCl gas was slowly bubbled into a suspension of 2,6-pyridinedicarboxylic acid (25 g, 0.15 mol, Aldrich Chemical Company) in 150 ml of methanol at room temperature. The suspension slowly turned into a clear solution with release of heat. The bubbling of HCl gas was stopped, the reaction flask tightly closed with a septum and stirred at room temperature in a well-ventilated hood. A white precipitate formed after about 40 min. After stirring at room temperature for 12 hr, the reaction mixture was concentrated under reduced pressure to give a white solid residue. The white solid was dissolved in methylene chloride (150 ml) and the organic layer washed with saturated $NaHCO_3$ solution (2×50 ml), dried ($MgSO_4$) and concentrated to afford the product 2 as a white solid (28.8 g, 98.5%): TLC: $R_f$0.36 (50% EtOAc in Hex); NMR ($CDCl_3$, 200 MHz) δ 4.02 (s, 6H), 8.01 (d, J=8 Hz, 0.5H), 8.04 (q, J=8 Hz, 0.5H), 8.32 (d, J=8 Hz, 2H).

EXAMPLE 2

Synthesis of Compound 3

The preparation of the mono alcohol from the diester was performed following the literature (Liren Huang, James C. Quada, Jr. and William Lown, Bioconjugate Chemistry, 1995, 6, 21–33). Reaction of diester (2, 14.1 g, 72.3 mmol) in 200 ml methanol with $NaBH_4$ (4.2 g, 0.11 mol) gave 8.3 g (69%) of product 3 as a white powder. TLC: $R_f$0.36 (EtOAc); NMR ($CDCl_3$, 200 MHz) δ 3.42 (br s, 1H), 3.99 (s, 1H), 4.85 (s, 2H), 7.52 (d, J=7.2, 1H), 7.84 (t, J=7.6 Hz, 1H), 8.03 (d, J=7.2 Hz, 1H).

EXAMPLE 3

Synthesis of Compound 4

To a solution of alcohol, 3 (3.4 g, 20 mmol) in 50 ml dry DMF was added imidazole (1.9 g, 28 mmol, 1.4 eq), followed by t-butyldimethylsilyl chloride (3.4 g, 22.6 mmol, 1.13 eq). The reaction was stirred at room temperature for 12 hr. The reaction mixture was diluted with EtOAc, the organic layer washed with water (5×30 ml) and concentrated to give the crude product as a sticky oil. Purification by silica gel flash column (20% EtOAc in Hex) then gave the product 4 as a white solid (5.3 g, 95%) and which had: TLC: $R_f$ 0.48 (25% EtOAc in Hex); NMR (CDCl$_3$, 200 MHz) δ 0.11 (s, 6H), 0.95 (s, 9H), 3.99 (s, 3H), 4.93 (s, 2H), 7.75 (dd, J=0.6, 7.8 Hz, 1H), 7.85 (t, J=7.8 Hz, 1H), 8.00 (dd, J=0.6, 8 Hz, 1H).

EXAMPLE 4

Synthesis of Compounds 5 and 5a

To a stirring solution of 4 (1.75 g, 6.2 mmol) in 20 ml THF/methanol (2/1) was added LiOH (monohydrate, 294 mg, 7 mmol, 1.1 eq, dissolved in ~1 ml water, heated to dissolve). The reaction was stirred at room temperature for 2 hr when TLC showed reaction was complete. The solvents were removed in vacuo, the residue treated with 10 ml of 1M H$_3$PO$_4$ (pH 3), the mixture shaken and the pH of the solution carefully re-adjusted to 3 with 1N HCl. The solution was extracted with dichloromethane (4×20 ml). The organic extracts were combined, dried (MgSO$_4$) and concentrated to give the protected acid (5) as a clear oil (1.4 g, 85%, slightly impure). The crude protected acid (380 mg, 1.4 mmol) was dissolved in 10 ml dry dichloromethane and to the stirring solution at room temperature was added N-hydroxysuccinimide (NHS) (242 mg, 2.1 mmol, 1.5 eq), followed by 1-(3-dimethyl-aminopropyl)-1-ethylcarbodiimide hydrochloride (EDCHCl) (355 mg, 1.85 mmol, 1.3 eq). The reaction was stirred at room temperature for 12 hr. The reaction mixture was concentrated to a volume of ~2 ml, and was directly loaded onto a silica gel column and eluted with 40% ethyl acetate in hexanes. The NHS ester (5a) was obtained as a white solid (210 mg, 41%) and which had: TLC: $R_f$ 0.55 (50% EtOAc in Hex); NMR (CDCl$_3$, 200 MHz) δ 0.12 (s, 6H), 0.95 (s, 9H), 2.91 (br s, 4H), 4.93 (s, 2H), 7.82–7.96 (m, 2H), 8.08 (d, J=8.0 Hz, 1H).

EXAMPLE 5

Synthesis of Compound 6

Compound 6 was prepared in a similar manner to that described in the literature. (A. J. Y. Lan, R. O. Heuckeroth, and P. S. Mariano, *J. Am. Chem. Soc.*, 1987, 109, 2738–2745).

To a stirring solution of alcohol, 3 (4.1 g, 24.6 mmol) in 100 ml dichloromethane and diethyl ether (1/1) at room temperature was added triphenylphosphine (7.1 g, 27.06 mmol, 1.1 eq), followed by carbon tetrabromide. The reaction was stirred at room temperature for 30 minutes. TLC showed a completed reaction. The reaction mixture was concentrated to remove most of the solvent. The residue was treated with EtOAc to precipitate triphenylphosphine oxide, and the EtOAc layer was decanted off. The procedure was repeated twice more. The EtOAc layers were combined and concentrated to give the crude product as an off-white slurry. Redissolution of the residue and purification by silica gel column chromatography afforded the title compound 6 as a white solid (5.4 g, 89%): TLC: $R_f$ 0.55 (50% EtOAc in Hex); NMR (CDCl$_3$, 200 MHz) δ4.00 (s, 3H), 4.63 (s, 2H), 7.68 (dd, J=1, 7.8 Hz, 1H), 7.86 (t, J=8 Hz, 1H), 8.06 (dd, J=1, 7.8 Hz, 1H).

EXAMPLE 6

Synthesis of Compound 7

Potassium t-butoxide (1.12 g, 10 mmol) was added under argon to a stirring solution of di-t-butyl-iminodicarboxylate (2.13 g, 9.8 mmol, Fluka) in 10 ml dry DMF at room temperature. The solution was stirred at room temperature for 30 minutes. To the stirring solution was added compound 6 (2.1 g, 8.5 mmol) in 8 ml dry DMF at room temperature. After stirring at 50° C. for two hr, the reaction mixture was concentrated in vacuo to remove most of the DMF. The residue was purified by silica gel column chromatography (30% EtOAc in Hex) to afford the product as a pale yellow oil (2.8 g, 86%) which solidified at room temperature after 10 hr: TLC: $R_f$ 0.66 (50% EtOAc in Hex); NMR (CDCl$_3$, 200 MHz) δ 1.42 (s, 18H), 3.98 (s, 3H), 5.01 (s, 2H), 7.3 (d, J=7.8 Hz, 1H), 7.80 (t, J=7.8 Hz, 1H), 8.00 (d, J=1, 7.6 Hz, 1H).

EXAMPLE 7

Synthesis of Compounds 8a and 8b

To a stirring solution of compound 7 (1.80 g, 4.7 mmol) in 20 ml THF/methanol (1/4) was added LiOH (monohydrate, 220 mg, 5.2 mmol, 1.1 eq, dissolved in ~1 ml water, heated to dissolve). The reaction was stirred at room temperature for 3 hr after which TLC showed the reaction was complete. The solvents were removed in vacuo, the residue treated with 8 ml 1M H$_3$PO$_4$ (pH 3) and the resulting solution extracted with dichloromethane (5×20 ml). The organic extracts were combined, dried (MgSO$_4$) and concentrated to give the product as an oil (1.45 g). NMR showed it to be a mixture of the mono-BOC compound (8a) (~80%) and di-BOC compound (8b) (~20%): δ 4.51 (d, J=6.2 Hz, BOC-NH—CH$_2$—), δ 4.97 (s, (BOC)$_2$N—CH$_2$—). The mixture was used for the next step without further purification.

EXAMPLE 8

Synthesis of Compound 10

To a stirring solution of BOC-glycyl-glycyl-OH, 9 (2.5 g, 10.8 mmol, Bachem Americas, Cat# A-1750) and N-hydroxysuccinimide (NHS) (1.49 g, 12.9 mmol) in 10 mL dry DMF in a 50-mL round bottom flask, was added 1-(3-dimethylaminopropyl)-3-ethylcarbodiimide hydrochloride (EDC.HCl) (2.2 g, 11.3 mmol, Aldrich). The reaction was stirred at room temperature for 3 hr. To the reaction mixture was added □-alanine benzyl ester p-toluenesulfonic acid salt (3.9 g, 11 mmol, Sigma) followed by dry diisopropylethylamine (1.55 g, 2.1 ml, 12 mmol). The reaction was stirred at room temperature for 14 hr. Most of the solvent (DMF) was removed under reduced pressure to leave a clear oil which was partitioned between 100 ml ethyl acetate and 20 ml water. The organic layer was separated and washed sequentially with water (1×20 ml), saturated NaHCO$_3$ solution, 1N HCl (2×15 ml) and water (1×10 ml); dried over MgSO$_4$ and concentrated to dryness to afford the product 10 as a white solid (3.8 g, 90%): TLC: $R_f$ 0.67 (1:2:2 MeOH/ CH$_2$C$_2$/EtOAc); NMR (CDCl$_3$, 200 MHz) δ 1.44 (s, 9H), 2.59 (t, J=6.2 Hz, 2H), 3.54 (q, J=6.2 Hz, 2H), 3.80 (d, J=5.8

Hz, 2H), 3.89 (d, J=5.6 Hz, 2H), 5.12 (s, 2H), 6.8 (br s, 1H), 6.85 (br s, 1H), 7.35 (m, 5H).

EXAMPLE 9

Synthesis of Compound 11

The protected dipeptide 10 (2.1 g, 5.3 mmol) was dissolved in 80 ml THF/EtOAc (1:1) with warming. HCl gas was then bubbled into the solution for about 5–10 minutes at room temperature and the resulting mixture stood at room temperature for 12–14 hr. The resulting white solid product (1.67 g, 95%) was filtered off, air-dried, then dried further under vacuum. The material had: NMR (D$_2$O, 200 MHz) δ 2.62 (t, J=6.4 Hz, 2H), 3.47 (t, J=6.6 Hz, 2H), 3.83 (s, 2H), 3.84 (s, 2H), 5.14 (s, 2H), 7.41 (br s, 5H).

EXAMPLE 10

Synthesis of Compound 12

To a stirring suspension of dipeptide HCl salt (11, 1.67 g, 5.1 mmol) in 15 ml dry THF and 3 ml dry pyridine at room temperature was added glutaric anhydride (600 mg, 4.9 mmol, Aldrich). The suspension was stirred at room temperature for 12 hr. The reaction mixture remained as a suspension throughout. The reaction mixture was concentrated to remove most of the THF and the residue was treated with 3 ml water to afford a clear solution. The solution was acidified with 6 N HCl (about 6 ml) whereupon the product precipitated out as a white solid. The solid was collected by filtration, washed with water (1×5 ml) and dried overnight under high vacuum to afford the title compound (12) as a white powder (1.77 g, 86%) and which had: NMR (CD$_3$OD, 200 MHz) 61.90 (m, 2H), 2.33 (t, J=7 Hz, 2H), 2.34 (t, J=7.2 Hz, 2H), 2.60 (t, J=6.8 Hz, 2H), 3.82 (d, J=5.8 Hz, 4H), 5.12 (s, 2H), 7.35 (br s, 5H); LC-MS: tR 8.98 min; Observed M+H 408.

EXAMPLE 11

Synthesis of Compound 14

Compound 14 was obtained in a similar manner to that described in European patent application EP 1 207 394 A2.

Compound 13 (1.5 g, 2.3 mmol, U.S. Pat. No. 5,196,438) in 100 ml methanol containing 0.16 g palladium on carbon (10% Pd—C, Aldrich) was hydrogenated at room temperature and atmospheric pressure for 4 hr. The reaction mixture was filtered through a CELITE pad in a fritted glass funnel. Concentration of the filtrate in vacuo afforded compound 14 (1.15 g, 97%) as a white solid: TLC: R$_f$ 0.25 (1:2:2 MeOH/ CH$_2$Cl$_2$/EtOAc) and coeluting with authentic material.

EXAMPLE 12

Synthesis of Compound 15

To a stirring solution of an ~80:20 mixture of compound 8a and 8b (0.19 g, ~0.75 mmol) in 15 ml dry dichloromethane were added sequentially NHS (115 mg, 1 mmol) and EDC HCl (175 mg, 0.91 mmol). The reaction mixture was stirred at room temperature for 40 minutes. To the reaction mixture was added compound 14 (260 mg, 0.5 mmol), followed by a catalytic amount of 4-dimethylaminopyridine (DMAP, ~10 mg). After stirring at room temperature for 4 hr, the reaction was concentrated and the residue dissolved in ~50 ml EtOAc. The organic layer was washed with water (1×10 ml), saturated NaHCO$_3$ solution (2×10 ml) and then concentrated to give crude product. Purification by silica gel column chromatography (70% EtOAc in Hex, then 10:40:50 MeOH/EtOAc/CH$_2$Cl$_2$) gave the intermediate N-protected product as a white solid [~260 mg, a mixture of mono-Boc (80%) and di-Boc (20%)]: TLC R$_f$ 0.62 (mono-BOC) and 0.69 (di-BOC), 1:2:2 MeOH/ CH$_2$Cl$_2$/EtOAc). The protected products were dissolved in 10 ml dichloromethane/TFA (1:1) and the solution was stirred at room temperature for 2 hr. The reaction was concentrated in vacuo and the residue partitioned between 20 ml dichloromethane and 10 ml saturated NaHCO$_3$ solution. The layers were separated and the aqueous layer was further extracted with dichloromethane (5×10 ml). The organic extracts were combined, dried (MgSO$_4$) and concentrated to afford the product 15 as a white solid (~210 mg): TLC R$_f$ 0.50 [70:28:2 CH$_2$Cl$_2$/MeOH/NH$_4$OH(aq 28%)]; LC-MS t$_R$ 10.13 mm, Observed M+H 650.

EXAMPLE 13

Synthesis of Compound 17

To a stirring solution of compound 12 (150 mg, 0.37 mmol) and NHS (56 mg, 0.48 mmol) in 2.5 ml dry DMF was added EDC.HCl (85 mg, 0.4 mmol). After stirring at room temperature for 5 hr, the reaction mixture was treated with a solution of 15 (150 mg, 0.23 mmol) and DMAP (2 mg) in 4 ml THF, and then was allowed to stir at room temperature for another 12 hr. The disappearance of starting material 15 and the formation of compound 16 were indicated by TLC and confirmed by LC-MS (t$_R$ ~12.0 min, observed M+H 1039.5). Small amounts of residual reagents and minor products were also observed. The reaction mixture containing crude compound 16 was diluted with methanol (3×30 ml), transferred to a 250 ml round-bottom flask and the contents hydrogenated in the presence of palladium on carbon (80 mg, 10% Pd—C) at room temperature and atmospheric pressure for 4 hr. The catalyst was removed by filtration through a pad of CELITE in a fritted glass funnel (4 μm). The filtrates were evaporated under reduced pressure, then under high vacuum, to remove solvents. The residue was purified by preparative RP-HPLC and the product fractions lyophilized to give compound 17 (95 mg) as an off-white solid, assigned as the trifluoroacetic acid salt.

A similar experiment performed in a similar manner gave identical material 17 and which had: LC-MS: t$_R$ 10.5 min, Observed M+H 949.5 (parent).

EXAMPLE 14

Synthesis of Compound 18

To a stirring solution of the acid 17 (85 mg, ~0.09 mmol) in 1 ml DMF and 2 ml acetonitrile was added NHS (62 mg, 0.54 mmol, 6 eq) and EDCHCl (103 mg, 0.54 mmol, 6 eq). The reaction was stirred overnight at room temperature. The disappearance of stating material and the formation of product 18 were indicated by LC-MS. The product mixture was directly purified by preparative RP-HPLC. The eluates containing product were combined and frozen, acetonitrile removed by high vacuum rotary evaporation (sublimation) onto a dry-ice/acetone cooling finger, and the residue lyophilized to give the product 18 as an off-white solid (39 mg), assigned as the trifluoroacetic acid salt.

A similar experiment performed in the same manner as above gave the same product 18 after RP-HPLC purification and lyophilization as above and which had: LC-MS $t_R$ 10.6 min, Observed M+H 1046.6 (parent); HR-ES MS: Calc M+H (parent) 1046.5306, observed 1046.5293.

EXAMPLE 15

Synthesis of Compound 19

To a stirring solution of compound 5a (200 mg, 0.55 mmol) in 10 ml dry dichloromethane was added compound 14 (210 mg, 0.4 mmol), followed by a catalytic amount of DMAP (~10 mg). After stirring at room temperature for 12 hr the reaction mixture was concentrated. The residue was dissolved in 25 ml of EtOAc and the organic layer washed sequentially with water (2×10 ml), saturated NaHCO$_3$ solution (2×10 ml) and concentrated. Purification by silica gel column chromatography then gave the intermediate TBDMS-protected product as a white solid (250 mg, 82%): TLC: $R_f$ 0.75 (1:2:2 MeOH/CH$_2$Cl$_2$/EtOAc). The white solid was dissolved in 10 ml acetonitrile and to the solution was added 0.5 ml 48% HF aqueous solution. After stirring at room temperature for 4 hr, the reaction mixture was diluted with 20 ml dichloromethane and washed with saturated NaHCO$_3$ solution (2×10 ml). The organic layer was concentrated and purified by silica gel column chromatography to afford the product 19 (180 mg, 85%) as a white solid and which had: TLC: $R_f$ 0.63 (1:2:2 MeOH/CH$_2$Cl$_2$/EtOAc); LCMS $t_R$ 11.2 min, Observed M+H 651.3; HR-ES MS: Calc M+H 651.3865, Observed 651.3872.

EXAMPLE 16

Synthesis of Compound 22

To a solution of 6-(FMOC)aminocaproic acid 20 (Advanced ChemTech, Louisville, Ky., USA; Cat # FX2650) (36 mg, 0.102 mmol) in dry methylene chloride (3 ml) was added NHS (13.1 mg) followed by EDCHCl (20.5 mg) and the reaction stirred overnight at room temperature under argon. LC-MS inspection of the reaction mixture indicated formation of the corresponding NHS ester product 21 as a single main peak ($t_R$ 15.7 min, observed M+H 451.2). The reaction mixture was divided into half. To one-half of the mixture was added compound 15 (45 mg, ~0.05 mmol as the di-trifluoroacetic acid salt) followed by triethylamine (21 μl, ~15 mg, ~0.15 mmol) and dry DMF (0.5 ml) to aid in dissolution of reactants. After 1.5 h inspection of the reaction by LC-MS showed formation of desired product with both starting materials still present. After stirring overnight at room temperature, LC-MS indicated formation of product together with side products. The reaction was diluted with 30–40 ml of CH$_2$Cl$_2$, washed sequentially with 0.1N HCl (twice), water (once), sat. NaHCO$_3$ (once), sat. NaCl (once), dried (Na$_2$SO$_4$), filtered and evaporated under reduced pressure. The residual liquid was redissolved in 5% MeOH in chloroform (CHCl$_3$) and purified by silica gel column chromatography (gradient of 5% to 10% MeOH in CHCl$_3$) to give the product 22 as a colorless/white glass (20 mg, 40%). The material had: TLC $R_f$ 0.42 (10% MeOH in CHCl$_3$); LC-MS $t_R$ 15.1 min, Observed M+H 985.5.

EXAMPLE 17

Synthesis of Compound 23

To a solution of compound 22 (20 mg, 0.0203 mmol) in dry CH$_2$Cl$_2$ (3.6 ml) was added piperidine (0.4 ml) and the reaction stirred at room temperature under argon. After 1.5 h inspection by TLC indicated reaction was complete. Volatile material was removed under reduced pressure, then under high vacuum at room temperature to give a residual white solid. The material was redissolved in acetonitrile (MeCN)— water with a small amount of trifluoroacetic acid (TFA) added in, filtered (0.45 m) and purified by preparative RP-HPLC [gradient of 5% (at 0 min) to 100% (at 20 min) of 0.1% TFA/MeCN in 0.1% TFA/H$_2$O]. Product fractions were combined, MeCN removed under reduced pressure, the aqueous residue frozen and lyophilized to give the product 23as a white solid, assigned as the di-TFA salt. The material had: LC-MS $t_R$ 10.3 min, observed M+H 763.4 (parent).

EXAMPLE 18

Synthesis of Compound 24

To a stirring semi-solution/suspension of terephthalic acid di-N-hydroxysuccinimide ester 28 [Ghoshal et al., EP 1,148, 339 A2] (3.2 mg, 0.0089 mmol) and 4 μL of triethylamine in 1.5 mL of dry CH$_2$Cl$_2$ was added dropwise a solution of 23 (8.8 mg, 0.009 mmol) in 1:2 chloroform—DMSO (0.75 mL) and the mixture stirred for a further 1.5 hr. Inspection by LC-MS indicated that the reaction was essentially complete. Volatile material was removed under high vacuum. The residue was dissolved in a little MeCN/water and purified by preparative RP-HPLC [C18; gradient of 5% (at 0 min) rising to 100% (at 20 min) of 0.1% TFA/MeCN in 0.1% TFA/water]. The main product peak was collected, frozen immediately, the acetonitrile sublimated off (high vacuum rotovap, dry-ice/acetone cold finger condenser) and the residue lyophilized to give the product 24 containing a little of the terephthaloyl bis-amide product. The material had: NMR: compatible; LC-MS: $t_R$ 12.4 min, observed M+H 1008.4. (bis-product at $t_R$ 13.0 min, observed M+H 1656.1)

EXAMPLE 19

Synthesis of succinimido-oxycarbonyl-ethylamino-glycyl-glycyl-glutaryl-aminomethyl-pyrsaquinavir Conjugate with KLH 25

To 20 mg of keyhole limpet hemocyanin (KLH, Pierce Biotechnology, Inc., Rockford, Ill., USA) reconstituted in 1.5 mL of 50 mM potassium phosphate buffer (KPi) pH 7.5 was added 0.5 mL of dimethylsulfoxide (DMSO) dropwise while cooling in an ice water bath and with stirring. One-quarter (0.5 mL) of the resulting solution (equivalent to 5 mg of KLH) was withdrawn for use as the standard/control. To the remaining solution of the protein (15 mg of KLH) was added compound 18 (6.5 mg, 5.1 μmol as di-TFA salt) dissolved in a total of 150 μL of DMSO. The cooling bath was removed and the mixture, in a capped vial, stirred overnight. The mixture was transferred to a dialysis cassette (Pierce Biotechnology, Inc; 10K molecular weight cutoff membrane; Product # 66425) and dialyzed sequentially against 30% (two changes), then 20%, then 10% DMSO in 50 mM KPi pH7.5 at ROOM TEMPERATURE, then against 50 mM KPi pH7.5 at ROOM TEMPERATURE, then against 50 mM KPi pH7.5 at ~4° C. (three changes). The KLH standard/control (vide supra) was similarly transferred to a smaller dialysis cassette (Pierce Biotechnology, Inc.) and dialyzed in the same manner. The retentates were removed from the cassettes to give the both the conjugate 25 as well as the standard/control as opalescent grey solutions. The concentration of the KLH standard/control was determined by UV using $A_{280}$=1.77 at 1 mg/mL. Coomassie Blue protein assay (modified Bradford) on the conjugate solution indicated 4.5 mg/mL of protein, using the KLH standard/control to construct a standard curve. trinitrobenzene-sulfonic acid assay (TNBS assay) on the conjugate solution indicated ~34% modification of available lysines, using the KLH standard/control as the comparison sample.

EXAMPLE 20

Synthesis of succinimido-oxycarbonyl-ethylamino-glycyl-glycyl-glutaryl-aminomethyl-pyrsaquinavir Conjugate with BSA 26

To a solution of 120 mg of bovine serum albumin (BSA) (Intergen Company, Purchase, N.Y., USA, Cohn Fraction V modified powder) in 4.0 mL of 50 mM potassium phosphate buffer (KPi) pH 7.5 was added 0.5 mL of dimethylsulfoxide (DMSO) slowly and dropwise. 0.75 mL of the resulting solution (equivalent to 20 mg of BSA) was withdrawn for use as the standard/control. To the remaining solution of the protein (100 mg of BSA) was added compound 18 (3.1 mg, 2.4 µmol as di-TFA salt) dissolved in a total of 300 µL of DMSO. The flask was capped and the reaction mixture stirred overnight. The mixture was transferred to a dialysis cassette (Pierce Biotechnology, Inc; 10K molecular weight cutoff membrane) and dialyzed sequentially against 20% (one change), then 10% DMSO in 50 mM KPi pH 7.5 at ROOM TEMPERATURE, then against 50 mM KPi pH7.5 at ROOM TEMPERATURE (one change), then against 50 mM KPi pH7.5 at ~4° C. (three changes). The BSA standard/control (vide supra) was similarly transferred to a smaller dialysis cassette and dialyzed in the same manner. The retentates were removed from the cassettes to give the both the conjugate 26 as well as the standard/control as clear solutions. The concentration of the BSA standard/control was determined by UV using $A_{280}$=0.6 at 1 mg/mL. Coomassie Blue protein assay (modified Bradford) on the conjugate solution indicated 11.2 mg/mL of protein, using the BSA standard/control to construct a standard curve.

EXAMPLE 21

Synthesis of succinimido-benzoyl-aminocaproyl-aminomethyl-pyrsaquinavir Conjugate with BSA 27

To a solution of 100 mg of bovine serum albumin (BSA) (Intergen Company, Purchase, N.Y., USA, Cohn Fraction V modified powder) in 2.0 mL of 50 mM potassium phosphate buffer (KPi) pH 7.5 was added 0.2 mL of dimethylsulfoxide (DMSO) slowly. 0.44 mL of the resulting solution (equivalent to 20 mg of BSA) was withdrawn for use as the standard/control. To the remaining solution of the protein (80 mg of BSA) was added compound 24 (2.7 mg, 2.4 µmol as TFA salt) dissolved in a total of 750 µL of DMSO. The flask was capped and the reaction mixture stirred overnight. The mixture was transferred to a dialysis cassette (Pierce Biotechnology, Inc; 10K molecular weight cutoff membrane; Product # 66425) and dialyzed sequentially against 30% (two changes), then 20%, then 10% DMSO in 50 mM KPi pH7.5 at ROOM TEMPERATURE, then against 50 mM KPi pH7.5 at ROOM TEMPERATURE, then against 50 mM KPi pH7.5 at ~4° C. (five changes). The BSA standard/control (vide supra) was similarly transferred to a smaller dialysis cassette and dialyzed in the same manner. The retentates were removed from the cassettes to give the both the conjugate 27 as well as the standard/control as clear solutions. The concentration of the BSA standard/control was determined by UV using $A_{280}$=0.6 at 1 mg/mL. Coomassie Blue protein assay (modified Bradford) on the conjugate solution indicated 14.5 mg/mL of protein, using the BSA standard/control to construct a standard curve. UV difference spectroscopy (against the BSA standard/control) indicated the presence of the hapten.

EXAMPLE 22

Antibody Development

All mice were kept in clear plastic cages, 5 to a cage, with stainless wire grid lids. The cage floor was covered with granulated dry corn cob bedding. Mouse chow dried pellet food was provided ad libitum, as was drinking water. Periodically, the water was replaced with grapefruit juice.

Female Balb/c mice, at least 3 months of age, were used for immunizations. The saquinavir conjugate with KLH (25) from Example 19 was emulsified in 50% complete Freund's adjuvant, 50% saline, at a final concentration of 100 µg/ml. Each mouse was injected with 100 µl in the peritoneal space. Thirty-five days later, similar injections were given in the same routes using Freund's incomplete adjuvant and the same concentration. Twenty-five days later, a third immunization was administered identical to the second formulation. The mice were allowed to rest (no further immunizations) for approximately 3 months. The mouse selected for use in fusion was given a booster immunization of the saquinavir-KLH conjugate identical to that of the second and third injections. Four days later, the mouse was used for cell fusion to develop monoclonal antibody secreting hybridomas.

The mouse selected for fusion was killed via exsanguination, and the spleen was harvested and ground between two sterile glass slides to release the lymphocytes. The resulting lymphocyte suspension was used to fuse with the F0 myeloma cell line (available from ATCC).

Fusion consisted of adding myeloma cells (⅕the number of lymphocytes), washing via centrifugation, resuspension in serum-free warm Iscove's modified Dulbecco's media (IMDM), and re-centrifugation. The centrifuge tubes containing the resulting pellets were gently tapped to loosen the cells, then 1 ml of warmed PEG/DMSO solution (Sigma Chemicals) was slowly added with gentle mixing. The cells were kept warm for 1.5 minutes, after which pre-warmed serum-free IMDM was added at the following rates: 1 ml/min, 2 min/min, 4 ml/min, 10 ml/min, then the tube was filled to 50 ml, sealed, and incubated for 15 minutes. The cell suspensions were centrifuged, the supernatant decanted, and IMDM containing 10% fetal calf serum was added. The cells were centrifuged once again and resuspended in complete cloning medium. This consisted of IMDM, 10% FCS, 10% Condimed H1 (Roche Molecular Systems), 4 mM glutamine, 50 µM 2-mercaptoethanol, 40 µM ethanolamine, and pen/strep antibiotics. The cells were suspended at a density of $4 \times 10^5$ lymphocytes/ml, distributed 100 µl/well into sterile 96-well microculture plates and incubated at 37° C. in 5% $CO_2$ for 24 hours. The next day, 100 µl of HMT selective medium (cloning medium+1:25 HMT supplement from Sigma Chemicals) was added. On the $6^{th}$ day of incubation, approximately 150 µl of media was drawn from each well using a sterile 8-place manifold connected to a light vacuum source. One hundred fifty microliters of HT media was then added. This consisted of cloning medium +1:50 HT supplement (Sigma Chemicals). The plates were returned to the incubator and inspected daily for signs of growth. When growth was judged sufficient, wells were screened for antibody production via ELISA.

Microplates were coated with 100 µl saquinavir-BSA conjugate (26) from Example 20 at 1 µg/ml in 0.1M carbonate buffer, pH 9.5 for 1 hour at 37° C. (humidified). The plates were then emptied and filled with a post-coat solution consisting of tris buffer, 1% gelatin hydrolysate, 2% sucrose, and 0.17% TWEEN 20 (all reagents from Sigma Chemicals). The plates were incubated for an additional 1 hour at 37° C. (humidified) after which they were washed with phosphate buffered saline containing 0.1% TWEEN 20. The plates were then filled briefly with a 2% sucrose solution in 0.15 M tris, pH 7.2–7.4, then emptied and allowed to air dry at room temperature. When dried, the plates were packed in zip-lock bags containing several desiccant pillows, sealed, and stored at 4° C. until use.

When the growing clones were judged ready for testing, 25 µl of supernatant from the wells were taken and transferred to 96-well flexible plates. Culture medium was added to each well to provide a 1:10 dilution of the media sample. Two saquinavir-BSA conjugate-coated wells were used for each culture well tested. One well received 50 µl of PBS buffer, the other received 50 µl of PBS containing saquinavir drug at a concentration of 800 ng/ml. Fifty microliters of the diluted sample were transferred to each of two of the coated wells above. The plates were incubated, covered, for 1 hour at 37° C. and then washed with PBS-TWEEN. The wells were then filled with 100 µl of goat anti-mouse IgG-HRP conjugate (Zymed Labs) diluted 1:5,000 in PBS-TWEEN and the plates reincubated for 1 hour. The plates were then washed again, and 100 µl of K-Blue substrate (Neogen Corp) was added. This was allowed to develop for 5–15 minutes, and the reaction was stopped by the addition of 100 µl of 1N HCl. Color was read via a microplate reader at 450 nm and collected by computer for analysis. Criteria for selection were binding to the saquinavir-BSA conjugate and significant inhibition of binding in the second well due to the free drug.

Subsequent to the selection of a clone from the fusion culture plates, the cells were subjected to stringent cloning via limiting dilution. Subclones growing from those wells in which single cells had been verified by microscopy were then re-tested by the above method. Stability of antibody expression was judged on the number of wells showing antibody, the level of binding, and the presence of any wells showing growth but little or no antibody. If any of the latter were found, a well showing high antibody secretion was then used to repeat stringent subcloning. This was repeated as necessary to obtain 100% of the subclones secreting equivalent quantities of antibody. Cells from selected wells were then expanded in culture and used to prepare preliminary cell banks. The supernatant from those cultures was then subjected to specificity analysis.

The antibody-containing culture supernatants from the expansion cultures were subjected to specificity analysis by the following procedure. First, the titer appropriate for analysis was determined by dilution analysis. A dilution of antibody providing for approximately 50% of maximal binding was selected for proceeding to the next step. Second, binding to the saquinavir-BSA conjugate was examined at the above antibody dilution in the presence of varying amounts of the most closely structurally related HIV protease inhibitor drug (nelfinavir) as well as two metabolites of saquinavir, M4 and M6. The data was subjected to analysis by non-linear regression curve fitting to a 4-parameter logistic function. That parameter which describes the concentration of the free drug which corresponds to 50% of the binding in the absence of free drug is termed the $ED_{50}$ for that drug. The specificity of the antibody can thus be described by comparing the $ED_{50}$ of the cognate drug, saquinavir, or saq $ED_{50}$, with the other values for other drugs fitted from those data according to the following equation (using nelfinavir data for this example):

$$\% \text{ cross-reactivity} = \frac{saq\ ED_{50}}{nel\ ED_{50}} \times 100$$

The four parameter logistic function used is $$OD_x = \frac{OD_{max}}{\left(1 + \left(\frac{ED_{50}}{X}\right)^s\right)} - OD_{min}$$

where S is the curvature parameter, $OD_{max}$ is the optical density with zero drug concentration, $OD_{min}$ is the optical density of the background of the instrument, and $OD_x$ is the optical density observed at drug concentration X in moles/liter (M/L). By this analysis, the cross-reactivities for two saquinavir antibodies are given in Table 2.

TABLE 1

Representative portion of plate screening

| Culture well | $OD_{450}$ in absence of free drug | $OD_{450}$ in presence of free drug |
|---|---|---|
| 19 F2 (SAQ 134) | 1.500 | 0.121 |
| 22 G5 (SAQ 137) | 1.526 | 0.083 |
| 47 H1 (SAQ 158) | 1.627 | 0.076 |
| 15 H6 (SAQ 221) | 1.699 | 0.295 |
| 27 G10 (SAQ 300) | 1.542 | 0.104 |

TABLE 2

Antibody specificity

| Clone | | Saquinavir | Nelfinavir | M4 metabolite | M6 metabolite |
|---|---|---|---|---|---|
| 300.1 | % Cross reactivity | 100 | <1 | 1.4 | <1 |
| | $ED_{50}$ (M/L) | $4.8 \times 10^{-9}$ | $>3 \times 10^{-8}$ | $3.4 \times 10^{-7}$ | $>3 \times 10^{-8}$ |
| 221.3 | % Cross reactivity | 100 | <1 | 5.8 | <1 |
| | $ED_{50}$ (M/L) | $6.0 \times 10^{-9}$ | $>3 \times 10^{-8}$ | $1.1 \times 10^{-7}$ | $>3 \times 10^{-8}$ |

TABLE 2-continued

Antibody specificity

| Clone | | Saquinavir | Nelfinavir | M4 metabolite | M6 metabolite |
|---|---|---|---|---|---|
| 137.3 | % Cross reactivity | 100 | <1 | <1 | <1 |
| | $ED_{50}$ (M/L) | $1.4 \times 10^{-8}$ | $>3 \times 10^{-8}$ | $>3 \times 10^{-8}$ | $>3 \times 10^{-8}$ |

EXAMPLE 23

Concentration Response

Antibody SAQ 137.3 was used to demonstrate concentration response for saquinavir in an ELISA assay format. The assay was carried out as described for specificity testing, with the modification that a greater number of concentrations were examined, and no other drugs were added. Table 3 lists the dose response, as optical density at 450 nm, provided by each concentration of saquinavir.

TABLE 3

Concentration response using SAQ 137.3

| Saquinavir conc. M/L | $OD_{450}$ |
|---|---|
| $2.98 \times 10^{-5}$ | 0.069 |
| $9.93 \times 10^{-6}$ | 0.078 |
| $3.31 \times 10^{-6}$ | 0.082 |
| $1.10 \times 10^{-6}$ | 0.100 |
| $3.68 \times 10^{-7}$ | 0.145 |
| $1.23 \times 10^{-7}$ | 0.240 |
| $4.09 \times 10^{-8}$ | 0.423 |
| $1.36 \times 10^{-8}$ | 0.670 |
| $4.54 \times 10^{-9}$ | 0.902 |
| $1.50 \times 10^{-9}$ | 1.029 |
| $5.05 \times 10^{-10}$ | 1.580 |
| $1.68 \times 10^{-10}$ | 2.192 |
| $5.61 \times 10^{-11}$ | 2.824 |
| $1.87 \times 10^{-11}$ | 2.967 |
| $6.23 \times 10^{-12}$ | 3.091 |

Murine hybridoma SAQ 137.3 was deposited with the American Type Culture Collection (ATCC) on Nov. 23, 2004 and assigned ATCC No. PTA-6329.

EXAMPLE 24

Synthesis of Compound 29

To a stirring solution of 5-nitroquinaldic acid (210 mg, 0.96 mmol) in 20 mL of $CH_2Cl_2$/acetonitrile (3:1) at RT under argon was added NHS (220 mg, 1.92 mmol) followed by EDC.HCl (236 mg, 1.16 mmol). After stirring for 1.5 h compound 14 (420 mg, 0.80 mmol) was added and the resulting mixture stirred overnight. The reaction was diluted with 40 mL EtOAc and washed sequentially with water (2×20 mL) and sat. aq. $NaHCO_3$ (2×10 mL), dried ($MgSO_4$), filtered and evaporated under reduced pressure. The residue was redissolved and purified by silica gel column chromatography, eluting with MeOH—EtOAc—$CH_2Cl_2$ (1:6:6), to give from the central cut of the main product band compound 29 as a light yellow solid (302 mg, 44%) after evaporation of solvent and drying under high vacuum. $^1$H-NMR: compatible. LC/MS: $t_R$ 13.5 min, observed M+H 716.3.

EXAMPLE 25

Synthesis of Compound 30

A solution of compound 29 (282.5 mg, 0.395 mmol) in 30 mL of MeOH was treated with 10% palladium on carbon (10% Pd—C) (165 mg) and the mixture hydrogenated at about 35 psi at RT for about 3 h with vigorous stirring. The catalyst was removed by filtration through CELITE® in a sintered glass funnel, washing the filter cake with MeOH. The combined filtrates were evaporated to dryness and the residue purified by silica gel column chromatography, eluting with MeOH—EtOAc—$CH_2Cl_2$ (1:4:5), to give from the central cut of the product band the compound 30 as a solid (170 mg, 63%). $^1$H-NMR: compatible. LC-MS: $t_R$ 12.3 min (0% to 100% of 0.1% TFA/MeCN in 0.1% TFA/water over 20 min; 1 mL/min), observed M+H 686.3.

In another run, hydrogenation (at ~35 psi) of 200 mg of compound 29 and 110 mg of 10% Pd—C in 20 mL of MeOH gave, after filtration of catalyst, evaporation and purification of the residue by preparative RP-HPLC, compound 30(60 mg) as the trifluoroacetic acid salt. LC-MS: $t_R$ 11.4 min, observed M+H 686.

EXAMPLE 26

Synthesis of Compound 31

Succinimido-oxycarbonyl-butyryl chloride, i.e., 5-(2,5-dioxo-1-pyrrolidinyl-oxy)-5-oxo-pentanoyl chloride, compound 34, was prepared according to Antonian et al., EP 0 503 454.

To a solution of the TFA salt of compound 30 (15 mg, 0.0164 mmol) in dry $CH_2Cl_2$ (3 mL) and dry DMF (0.1 mL) was added the bifunctional linker compound 34 (4.3 mg, ~3 mol. equiv.) and the reaction stirred at RT for about 3 h under argon. Analysis by analytical RP-HPLC indicated product together with substantial amounts of a faster-running substance as well as smaller amounts of other substances. Solvent was removed under high vacuum (rotovap), the residue redissolved in a small volume of MeCN/water (1:1) and purified by RP-HPLC. The product peaks (second major peak) were combined, immediately frozen (dry ice/acetone bath), the acetonitrile sublimated off on a high vacuum rotovap equipped with a dry-ice/acetone cooling finger, and the still-frozen largely aqueous residue lyophilized normally to give the product compound 31 as a pale yellow solid (4.2 mg). $^1$H-NMR: compatible. LC-MS: $t_R$ 12.4 min, observed M+H 897.4.

EXAMPLE 27

Synthesis of Compound 32

A mixture of compound 30 (25 mg, 0.036 mmol) and compound 34 (14 mg, 0.057 mmol) in about 2 mL of dry $CH_2Cl_2$ was stirred at RT under argon for about 3 h then stood at about 4° C. overnight. The reaction was warmed back up to RT and solvent removed under reduced pressure to give a residue containing crude compound 31.

The material was redissolved in dry DMF (5 mL) and Glycyl-Glycyl-β-Alanine (Bachem California Inc., Torrance, Calif., USA; Cat# H-3295) (15 mg, 0.074 mmol) added as a solid. The stirring mixture was heated at 80° C.

overnight under a reflux condenser and under argon. Analytical RP-HPLC indicated formation of desired product as the major peak. Solvent was removed under high vacuum (high vac rotovap), the residue redissolved in about 1.5 mL MeCN/water and purified by RP-HPLC. The product fractions were combined, MeCN removed under reduced pressure, the aqueous residue frozen and lyophilized to give the product 32 as a solid (23 mg, 64% overall). $^1$H-NMR: compatible. LC-MS: $t_R$ 10.5 min, observed M+H 985.5.

EXAMPLE 28

Synthesis of Compound 33

To a stirring solution of compound 32 (18.1 mg, 0.0184 mmol) in 1 mL of dry $CH_2Cl_2$ and 1 mL of dry DMF was added NHS (2.6 mg, 0.0226 mmol) and EDC.HCl (3.9 mg, 0.0203 mmol) and the reaction stirred at RT under argon, following by analytical RP-HPLC. After stirring overnight, additional NHS (2.6 mg) and EDC.HCl (3.9 mg) were added and the reaction stirred for an additional 4 h at RT. Analytical RP-HPLC indicated essentially complete reaction with formation of desired product with a small amount of starting acid left. Solvent was removed under high vacuum, the residue redissolved in 1:1 MeCN/water and purified by preparative RP-HPLC to give the product peak: $t_R$ 11.0 min, observed M+H 1082.6; sensitive to hydrolysis.

EXAMPLE 29

Synthesis of Compound 35

Reduction of 2-methoxycarbonyl-4-chloro-6-nitroquinoline, compound 34 (Maybridge CombiChem, Maybridge PLC, Tintagel, Cornwall, United Kingdom; Cat # SEW 05145) with stannous chloride in ethanol containing aq. HCl was performed following the literature method (Royer, R. *J. Chem. Soc.*, 1949, 1803; Bellamy, F. D. and Ou, K. *Tetrahedron Letters*, 1984, 25, 839–842) to give compound 35 as a dark red solid, used without further purification.

EXAMPLE 30

Synthesis of Compound 38

Crude compound 35 (0.68 g) was dissolved in 10 ml 50% methanol in ethyl acetate and to the solution was added $(BOC)_2O$ (865 mg, 4 mmol), followed by DMAP (40 mg, 0.3 mmol). After stirring at RT for 8 hr, the reaction mixture was concentrated and directly purified by silica gel column chromatography, eluting with EtOAc/hexanes (1:1) to give the mono-BOC compound 36a (100 mg) and the di-BOC compound 36b (120 mg). TLC: $R_f$ 0.33 (compound 36a and 0.59 36b, 50% EtOAc in hexanes). $^1$H-NMR: compatible for both.

The mono- and di-BOC-protected compounds 36a and 36b (recombined mixture, 160 mg) was dissolved in 10 mL methanol and saponified with LiOH (43 mg, monohydrate, 1 mmol, dissolved in 0.5 mL water) for 4 h. The reaction mixture was concentrated, the residue treated with 2.5 mL of 1N HCl, and extracted with EtOAc (2×10 mL). The extracts were combined, dried ($MgSO_4$) and concentrated in vacuo to afford the product as a yellow solid (150 mg) containing the mono-BOC compound 37a and the di-BOC compound 37b as a 2:1 mixture by $^1$H-NMR and LC-MS. The mixture was used in the next step without further purification. LC-MS: compound 37a: $t_R$ 13.7 min, observed M+H 323.1; compound 37b: $t_R$ 15.6 min, observed M+H 423.1.

The mixture of 37a and 37b from above was dissolved in 5 mL dry THF and to the stirring solution was added NHS (58 mg, 0.5 mmol) followed by EDC.HCl (83 mg, 0.43 mmol). After stirring at RT for 2 h, the reaction mixture containing the corresponding NHS ester was treated with compound 14 (247 mg, 0.38 mmol) and DMAP (10 mg). The resulting mixture was stirred at RT for a further 12 h and was then concentrated under reduced pressure. The residue was treated with 10 mL TFA and the solution stirred at RT for 4 h. TFA was removed in vacuo and the residue was purified by preparative RP-HPLC to afford compound 38 as a brownish solid (34 mg).

$^1$H-NMR: compatible. LC-MS: $t_R$ 12.7 min, observed M+H 720.3.

EXAMPLE 31

Synthesis of Compound 39

Compound 38 is reacted with compound 34 in a similar manner to that used to synthesize compound 31 and is purified in a similar manner to give compound 39.

What is claimed is:

1. A compound having the structure

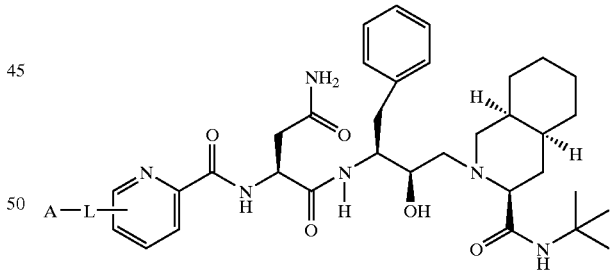

I wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

2. The compound of claim 1 wherein A is an active ester.

3. The compound (18) having the structure

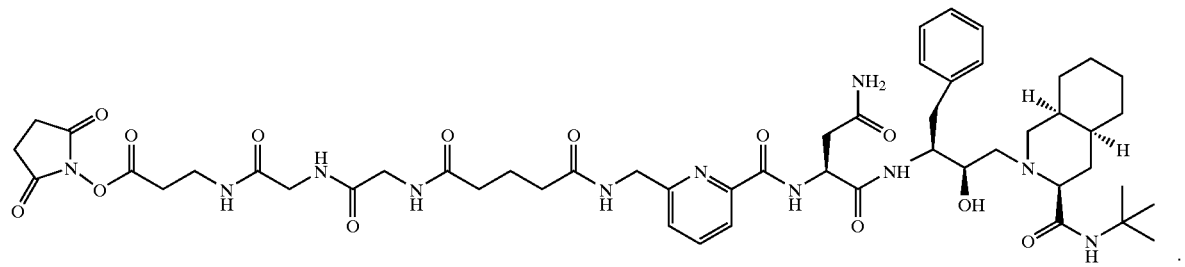

4. A compound having the structure

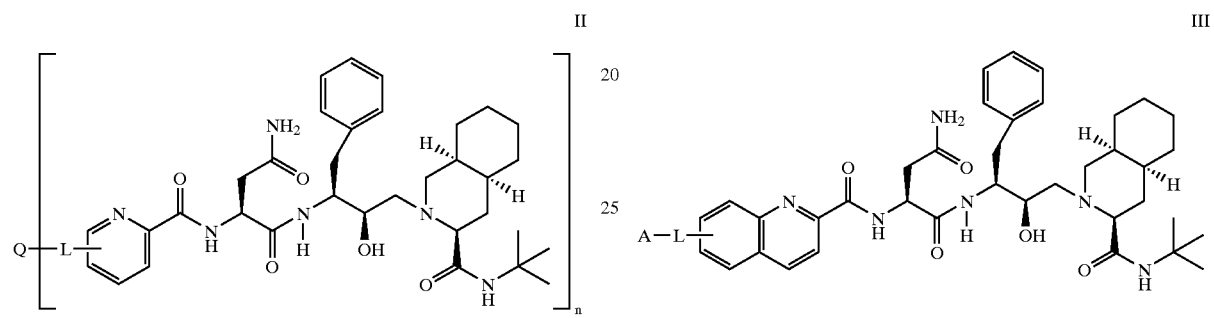

wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and Q is selected from the group consisting of polypeptides, polysaccharides, synthetic polymers, and non-isotopic labels, and n is a number from 1 to 50 per kilodaltons molecular weight of Q.

5. The compound of claim 4 wherein Q is selected from the group consisting of bovine serum albumin, keyhole limpet hemocyanin, and aminodextran.

6. The compound succinimido-oxycarbonyl-ethylamino-glycyl-glycyl-glutaryl-aminomethyl-(pyr)saquinavir conjugate with KLH (25).

7. The compound succinimido-oxycarbonyl-ethylamino-glycyl-glycyl-glutaryl-aminomethyl-(pyr)saquinavir conjugate with BSA (26).

8. The compound succinimido-benzoyl-aminocaproyl-aminomethyl-(pyr)saquinavir conjugate with BSA (27).

9. A compound having the structure wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

10. The compound of claim 9 wherein A is an active ester.

11. A compound having the structure

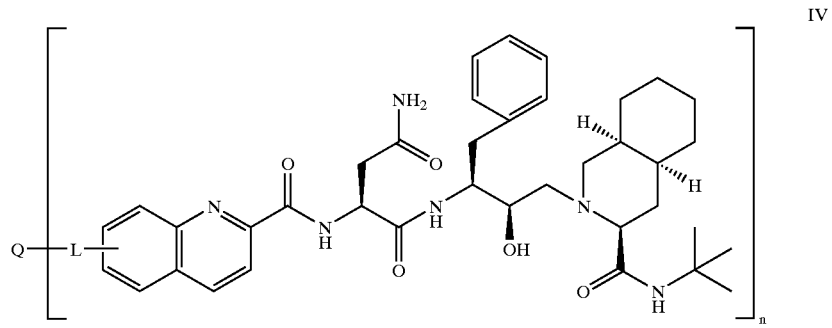

wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and Q is selected from the group consisting of polypeptides, polysaccharides, synthetic polymers, and non-isotopic labels, and n is a number from 1 to 50 per kilodaltons molecular weight of Q.

12. The compound of claim 11 wherein Q is selected from the group consisting of bovine serum albumin, keyhole limpet hemocyanin, and aminodextran.

13. An antibody generated in response to a compound having the structure:

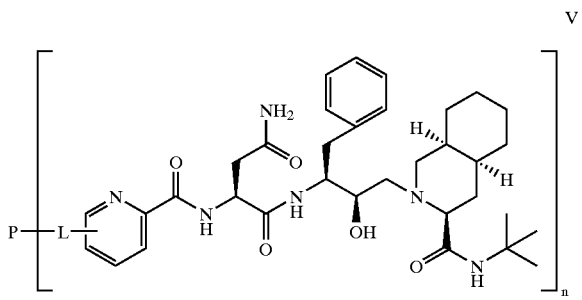

V wherein L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, P is a polypeptide, and n is a number from 1 to 50 per kilodaltons molecular weight of P.

14. A monoclonal antibody specific for saquinavir having less than 1% cross-reactivity with nelfinavir and with saquinavir metabolites M4 and M6.

15. Murine hybridoma SAQ 137.3 having ATCC No. PTA-6329.

* * * * *